United States Patent
Kain et al.

(10) Patent No.: US 9,327,040 B2
(45) Date of Patent: May 3, 2016

(54) OZONE SANITIZING SYSTEM

(71) Applicant: GLOBAL OZONE INNOVATIONS, LLC, Elkhart, IN (US)

(72) Inventors: Rikki F. Kain, Elkhart, IN (US);
Michael A. Engle, Elkhart, IN (US);
Donald Ray Fraser, Goshen, IN (US)

(73) Assignee: Global Ozone Innovations, LLC, Elkhart, IN (US)

( * ) Notice: Subject to any disclaimer, the term of this patent is extended or adjusted under 35 U.S.C. 154(b) by 0 days.

(21) Appl. No.: 14/488,643

(22) Filed: Sep. 17, 2014

(65) Prior Publication Data
US 2015/0004061 A1  Jan. 1, 2015

Related U.S. Application Data

(63) Continuation of application No. 13/737,191, filed on Jan. 9, 2013, now Pat. No. 8,865,065.

(51) Int. Cl.
*A61L 9/00* (2006.01)
*B60H 3/00* (2006.01)
*B01L 1/04* (2006.01)
*A61L 2/20* (2006.01)
*A61L 2/24* (2006.01)

(52) U.S. Cl.
CPC . *A61L 2/202* (2013.01); *A61L 2/24* (2013.01);
A61L 2202/14 (2013.01)

(58) Field of Classification Search
CPC ........... A61L 2/00; A61L 2/183; A61L 2/202;
A61L 9/00; A61L 9/015; A61L 9/03; A01N 1/0215

USPC ........... 422/1, 3, 5, 28, 30, 33, 105, 119–120,
422/186.07, 292, 305–306; 454/156, 187;
96/223, 226–227
See application file for complete search history.

(56) References Cited

U.S. PATENT DOCUMENTS

| 4,244,712 | A | 1/1981 | Tongret |
| 4,978,530 | A | 12/1990 | Strong |
| 5,839,155 | A | 11/1998 | Berglund et al. |
| 6,759,006 | B1 | 7/2004 | Siklosi et al. |
| 6,889,449 | B2 | 5/2005 | Silver |
| 6,936,434 | B2 | 8/2005 | McDonnell et al. |

(Continued)

OTHER PUBLICATIONS

Office Action Dated Mar. 27, 2014—U.S. Appl. No. 13/737,191, filed Jan. 9, 2013—Title—Ozone Sanitizing System.

*Primary Examiner* — Monzer R Chorbaji
(74) *Attorney, Agent, or Firm* — Woodard, Emhardt, Moriarty, McNett & Henry LLP

(57) ABSTRACT

A device for sanitizing objects using ozone is disclosed having a container defining an enclosed space and a selectively closeable opening for enclosing the space, an ozone generator, an ozone converter, a controller, and a timer working together to generate a predetermined concentration of ozone within the enclosed space and maintain approximately the same concentration for a predetermined period of time. Also disclosed are assemblies and methods detecting and warning of entrapment within the enclosure and halting ozone production when it occurs. Further disclosed are devices and methods for coupling a maintenance device to the sanitizing system to perform various maintenance operations such as adjusting operational control parameters, and observing conditions within the enclosed chamber in real-time such as temperature, humidity, and ozone concentration.

23 Claims, 14 Drawing Sheets

(56) References Cited

U.S. PATENT DOCUMENTS

| | | |
|---|---|---|
| 7,279,452 B2 | 10/2007 | Svendsen et al. |
| RE40,495 E | 9/2008 | Svendsen |
| 7,886,392 B2 | 2/2011 | Wong et al. |
| 8,261,389 B2 | 9/2012 | Yoo et al. |
| 2011/0002810 A1* | 1/2011 | Watson .................. A61L 2/202 422/5 |

* cited by examiner

OZONE SANITIZING SYSTEM

CROSS-REFERENCE TO RELATED APPLICATION

This application is a continuation of application Ser. No. 13/737,191, filed Jan. 9, 2013, which is hereby incorporated by reference in its entirety.

BACKGROUND

Bacterial infections and the spread of viruses is an ever growing health concern. Numerous ways exist to kill bacteria which require direct contact between an oxidant and the virus or bacteria and many commercial products claim a 99.99% kill rate of these microorganisms. In order to fulfill these claims, these products must contact 99.99% of the target microorganisms. However, achieving direct contact with all of the microorganisms is difficult due first of all to the nature of the materials locations where they are found such as clinging to clothing fibers, utensils, tools, and other common devices having large surface areas with numerous cracks, grooves, and hidden locations for bacteria and viruses to congregate. Furthermore, it has been shown that bacteria cells have a tendency to clump together, thus protecting cells inside the clump from the oxidant resulting in some number of cells that are difficult to kill.

One effective technique for obtaining a satisfactory kill rate of both bacteria and viruses is to immerse the object in ozone gas which disinfects and effectively eliminates the bacteria as well as reducing the advantage gained by the clumping effect. Ozone ($O^3$) is effective because it is a strong oxidant and disinfectant, being more effective than hydrogen peroxide or bleach and iodine, and does not leave any residue or odor. Ozone is naturally occurring and can be used to purify air, water, and some foods. For example, it is used in conjunction with water treatment to rid water of hazardous pathogens including chlorine resistant cryptosporidium and is also used as an alternative disinfectant for water sensitive produce.

Ozone destroys bacteria by interfering with the metabolism of bacterium cells and in sufficient quantities, ozone will break through the cell membrane and lead to the destruction of the bacteria. Ozone also destroys viruses by diffusing through the protein coat resulting in damage to the viral RNA. For example, ozone has been shown to be effective in destroying Methicillin-Resistant *Staphylococcus Aureus* (MRSA), *Shaphylococcus Aureus* (Staph) and Candida virus. Kill rates of 99.99% have been demonstrated in these bacteria when exposed ozone for 10 seconds to 8 min. with ozone concentrations between 300 and 1500 ppm.

Thus ozone has proven to be an efficient and effective sanitizing substance capable of killing bacteria and viruses. However, due to the powerful oxidizing properties that make it a strong sanitizing agent, ozone is also a powerful irritant for humans, affecting especially the eyes and respiratory systems and can be hazardous. Even low concentrations of ozone can be harmful to the upper respiratory tract and the lungs. The severity of injury depends on both by the concentration of ozone and the duration of exposure. Therefore, the U.S. Occupational Safety and Health Administration (OSHA) the National Institute of Occupational Safety and Health (NIOSH) have both established exposure limits (PEL) for work environments where ozone is used or where it is likely to be produced.

SUMMARY

The embodiments disclosed include a sanitizing system as well as methods of operation, and methods of maintaining such a system. Disclosed is a cabinet, box, or other similar enclosure within which an object to be disinfected is placed. The object is enclosed, preferably within a substantially hermetically sealed interior space defined by the cabinet which is filled with ozone gas, for example by generating ozone within the enclosed space, until a predetermined concentration is reached. The predetermined concentration of ozone gas is then maintained for a predetermined period of time to effectively "soak" the contents of the enclosed cabinet in ozone gas thereby achieving the desired effect of destroying various viruses, bacteria, and other biological agents susceptible to destruction by a strong oxidant such as ozone. A controller responsive to a sensor positioned inside the cabinet is also envisioned to assist in maintaining the predetermined concentration of ozone within the interior chamber of the cabinet with the controller being responsive to the sensor to control an ozone generator to generate more ozone if the concentration falls below a predetermined level. A timer is also included to manage the period of time various activities are allowed to continue, such as the ozone generation, soak duration, and others.

Also included are embodiments of methods of operating the device including at least one embodiment of logical flow used by the controller to activate and deactivate various indicators, and to automatically lock and unlock the door in response to signals from the controller to maintain a safe environment for the operator. For example, the controller will preferably not allow the lock to be electronically released and the door opened until the conversion process has reduced the concentration of ozone within the interior of the cabinet to a predetermined minimum concentration or "safe" level. Also included is an entrapment sensor and accompanying control logic that will not allow the device to generate ozone if entrapment or foreign object is detected. For example if an object exerts sufficient weight against the floor of the device to trigger a switch, entrapment logic is triggered and ozone production is halted or not allowed until the object pressing against the floor is removed.

The conversion process and logic to activate it is also disclosed whereby the ozone conversion to diatomic oxygen is accelerated within the chamber until the ozone has been reduced to a safe level at which time the door can be unlocked and the device opened allowing the now sanitized object or objects to be removed from the chamber. One embodiment of a control panel is also included with various embodiments of indicators to indicate the progress of the device throughout the sanitizing procedure including the conversion process as well as controls for starting and stopping a sanitizing cycle which includes an initial ozone generation phase, a soak phase, and an ozone conversion phase.

Also included are embodiments of a method of maintaining a sanitizing system including connecting a maintenance device and adjusting system parameters, operating parameters, and obtaining real-time information about the operating state of the system during operation such as the current temperature, humidity, and ozone concentrations within the chamber, as well as time remaining in the current cycle, and other similar information. Also disclosed are methods for adjusting the parameters and including modifying the logic used by the controller to operate the device.

Various forms, objects, features, additional aspects, advantages, and embodiments will become apparent to those of ordinary skill in the art from the following detailed description when read in light of the accompanying drawings.

DETAILED DESCRIPTION

Figure 1:
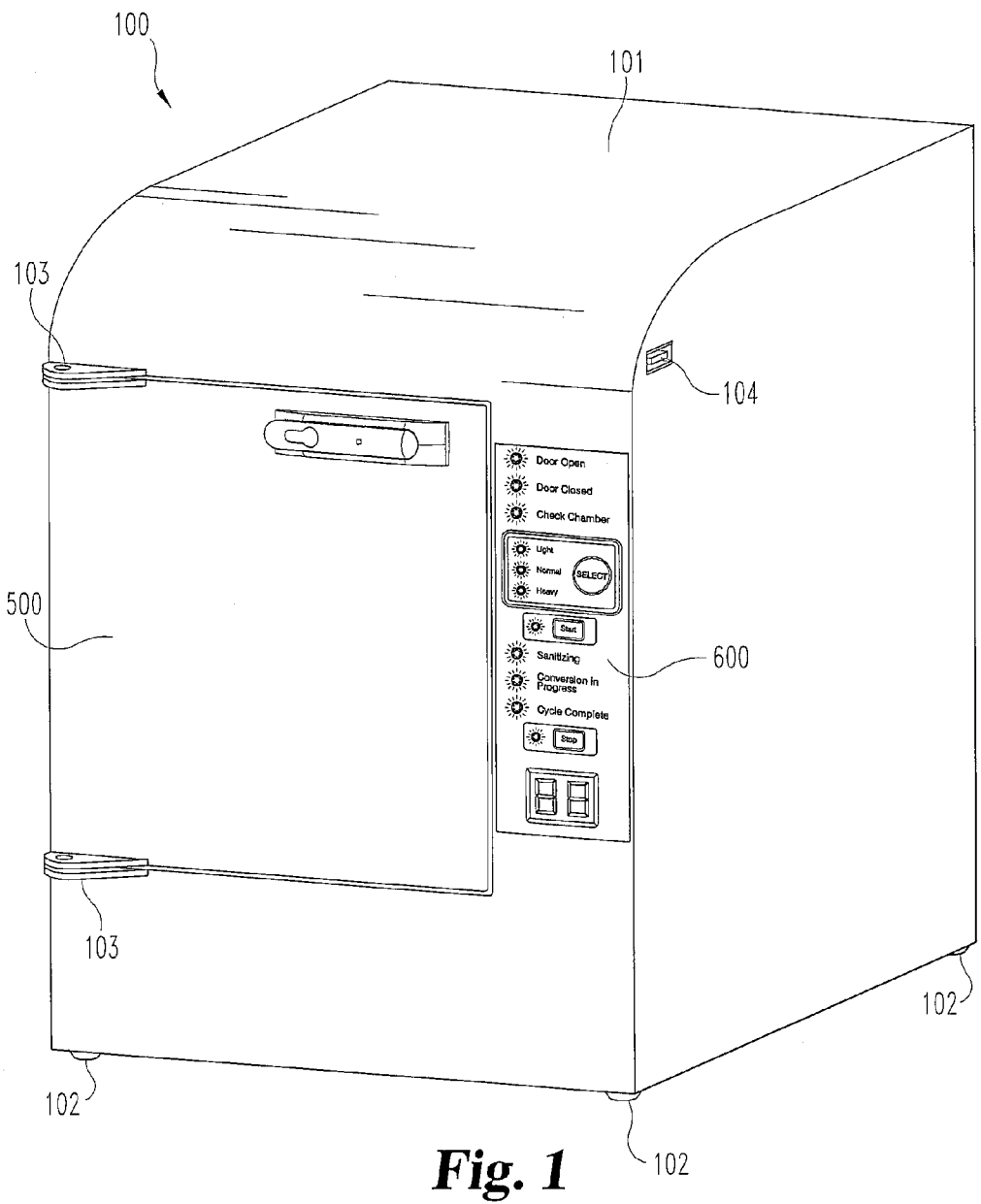
FIG. 1 is a perspective view of one embodiment of a sanitizing system.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

One embodiment of an ozone sanitizing system 100 is illustrated in FIGS. 1 through 5 and described below. FIG. 1 shows a perspective view of the sanitizing system 100 adapted for use in a device having a cabinet 101 which serves as an outer enclosure or outer container within which a second inner container (see FIG. 2) may be enclosed, the second container defining an interior enclosed space. The device embodied in FIG. 1 also includes a door assembly 500 rotatably mounted to cabinet 101 using rotatable coupling devices such as hinges 103. Thus in the embodiment illustrated in FIG. 1, door assembly 500 operates as a selectively closeable opening providing access to the enclosed interior spaces defined by the inner and outer containers of cabinet 101 (see FIG. 5). Sanitizing system 100 further includes a control panel 600 for accepting user input to control the device. The control panel is discussed in greater detail below (see FIG. 6) and may include various indicators, buttons, knobs, and other similar controls. Cabinet 101 preferably rests on supports 102 which operate to support cabinet 101 above a supporting surface. One embodiment of supports 102 include unitary objects positioned to provide support. Other embodiments of supports 102 may also operate as leveling devices by, for example, being adjustable in length thus allowing separate supports 102 to be lengthened or shortened as necessary to level cabinet 101 on an uneven surface.

Sanitizing system 100 also includes a connection port 104 in cabinet 101 useful for coupling a device useful for performing maintenance on sanitizing system 100. Connection port 104 can be used to transfer operating parameters, system logic, and other useful information between a maintenance device coupled to connection port 104 and a controller which controls the function of sanitizing system 100 (as discussed below with respect to FIGS. 13 and 14). Sanitizing system 100 in the preferred embodiment operates using electrical power which is controlled by a power switch 105 (see FIG. 2). In one embodiment, power switch 105 is a power switch able to stop the flow of electricity when switched off by the user, and able to begin the flow of electricity when switched on by the user. In another embodiment, power switch 105 includes an automatic circuit interrupting device such as a circuit breaker or fuse that is able to stop the flow of electricity in situations where an abnormal surge in power consumption occurs.

Figure 2:
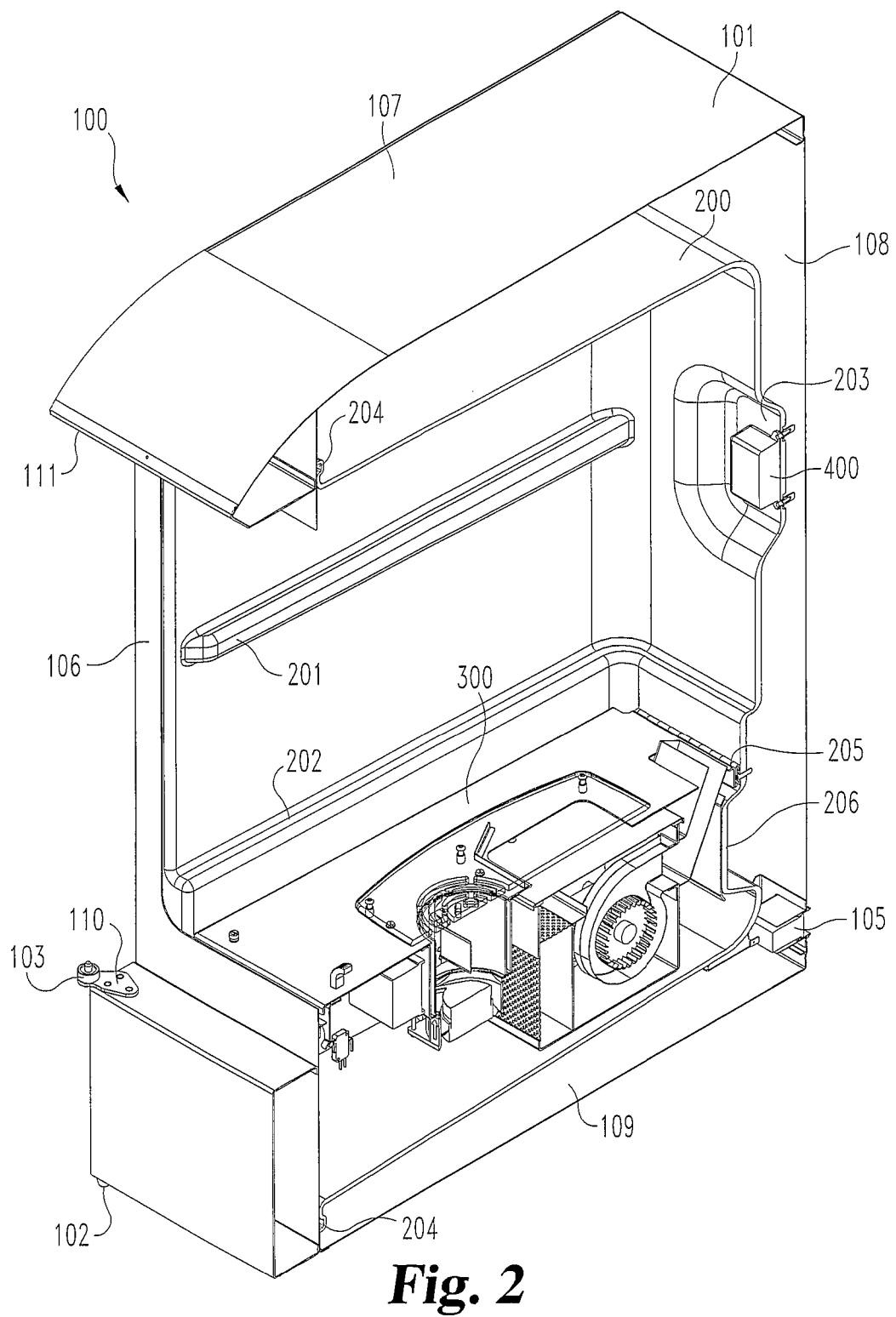
FIG. 2 is a cutaway perspective view showing further detail of the embodiment from FIG. 1.

FIG. 2 illustrates further detail of the sanitizing system 100 shown in FIG. 1. Cabinet 101 forms a first outer container of sanitizing system 100 with a top 107, a back 108, and a bottom 109, along with a case 106 that is configured to cover the remaining three sides covering a second inner container 200. In the embodiment of FIGS. 1 and 2, inner container 200 serves to form a second inner container, or inner chamber, for containing the ozone and the items to be sanitized during the sanitizing procedure. A selectively closeable opening, embodied in FIG. 1 as door assembly 500, has been removed in FIG. 2 to expose further detail of the interior spaces enclosed within device 100. Hinges 103 shown in FIG. 1 rotatably mount door assembly 500 to cabinet 101 at an upper hinge mount would otherwise appear mounted in upper hinge mount 111 (hinge not shown in FIG. 2), and a lower hinge mount 110, where a lower mounted hinge 103 is shown in position in FIG. 2.

As previously noted, cabinet 101, serves as an outer enclosure containing an inner container 200 shown in FIG. 2 thus creating a double shell or double wall containment unit. In one embodiment, inner container 200 is constructed of a unitary piece of material formed or molded from a polymeric material or metal or similar substance operable to maintain fluids under pressure. In another embodiment, inner container 200 is formed of several pieces of polymeric material or metal molded, adhered, welded, or otherwise fastened together to form a container operable to maintain fluids under pressure without substantial leakage through the material. Any suitable material may be used such as various types of metals include aluminum, steel, and the like, or various alloys of these and other metals. Preferably the inner container 200 is formed from a polymeric material such as a plastic like polyethylene terephthalate, polyethylene, high-density polyethylene, polyvinyl chloride (pvc), low-density polyethylene, polypropylene, polystyrene, high impact polystyrene, polyamides, acrylonitrile butadiene styrene, polyethylene/acrylonitrile butadiene styrene, polycarbonate, or polycarbonate/acrylonitrile butadiene styrene, any of which may or may not include strengthening members or meshes to increase strength and rigidity.

In the preferred embodiment shown in FIG. 2, inner container 200 defines an interior enclosed space accessible by an opening embodied in FIG. 2 as the open side of inner container 200. In order to provide for substantial hermetic seal for this opening, inner container 200 is mounted to the interior side of case 106 and includes a gasket 204 positioned between the portion of inner container 200 in contact with case 106 and case 106 itself. Gasket 204 thus operates as a sealing member to substantially hermetically seal the junction between the inside surface of case 106 and inner container 200 to avoid any substantial leakage of ozone during operation of the system. Inner container 200 is maintained in position to provide the seal along gasket 204 by any of various means known to one of ordinary skill in the art such as various types of fasteners including one or more bolts, screws, pins, and may also include adhesives, chemical bonding, friction fit, or any other suitable method or combination thereof for joining and fastening inner container 200 to mount and retain it in a substantially hermetically sealed position in relation to case 106.

Inner container 200 also includes mounts for racks, shelves, baskets, or other containers or devices for holding items to be sanitized within the enclosed space defined by inner container 200. As shown in FIG. 2, a first mount 201 and a second mount 202 are included within inner container 200 as molded or formed along with inner container 200 during its construction. However, other embodiments are envisioned such as one or more cleats, pegs, fasteners, hangers, hooks, or any other suitable mounting device coupled to the interior walls of inner container 200 that may be used to mount a device or container for holding items to be sanitized, or for holding the items to be sanitized themselves. In another embodiment, the enclosed space defined by container 200 has no hooks, hangers, fasteners, baskets, or containers as discussed above but is an empty cavity for placing items to be sanitized without any additional mounts or similar such devices for separating the items or organizing them.

Timer container 200 also includes other mounting areas for various purposes such as a sensor mount 203 for positioning a sensor assembly 400 that is preferably configured within inner container 200 in a location from which accurate measurements of the current state of the atmosphere within inner container 200 can be obtained such as temperature, humidity, and ozone levels, and possibly other current state values as well. Likewise, inner container 200 also contains a floor assembly 300 that is rotatably or removably coupled to inner container 200 by a floor mount 205. Floor mount 205 includes a nondestructively removable mount such as a hook, clasp, latch, or any combination or series thereof, or a hinge or series of hinges. In this embodiment, floor assembly 300 may be raised for easy access to the component parts of floor assembly 300 for inspection or maintenance of the ozone generator and other components which are coupled to the floor and discussed in greater detail below with respect to FIG. 3. Also, an ozone converter assembly mount 206 is included in inner container 200 which provides a mounting location for the ozone converter which in the illustrated embodiments is not coupled to the floor but to converter assembly mount 206.

Figure 3:
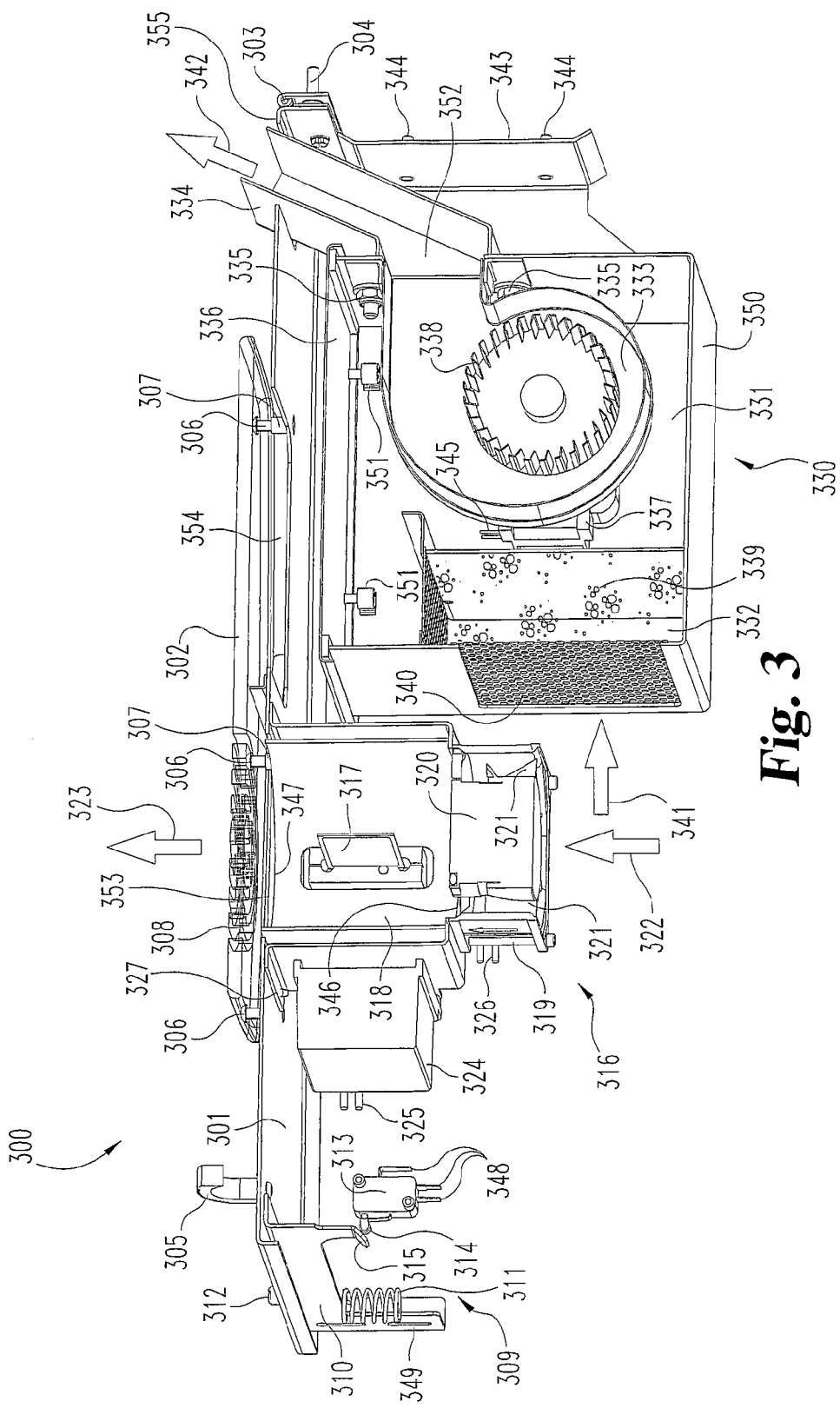
FIG. 3 is a cutaway perspective view showing further detail of the embodiment shown in FIG. 2.

Further details of the operational components and subassemblies of sanitizing system 100 are shown in FIG. 3. A floor assembly 300 is illustrated having a floor 301, a floor support assembly 309 and an ozone generator assembly positioned along with an ozone converter assembly 330. Floor 301 operates as a horizontal support member and provides structure for mounting or for enclosing many of the other subassemblies shown in FIG. 3. Floor 301 may be constructed of one or more rigid members extending across the lower region of the inner container 200 separating inner container 200 into a first region above floor 301 preferably containing the items to be sanitized, and a second region below floor 301 preferably containing the devices and machinery for generating and converting ozone and not containing the items to be sanitized. Floor 301 is mounted to floor mount 205 (shown in FIG. 2) using a corresponding floor mounting assembly 303. Parts of floor mounting assembly 303 are coupled to floor mount 205 using floor mounting fasteners 304 which may include one or more bolts, screws, pins, retained alone or in combination with adhesives, chemical bonding, friction fit, or any other suitable method or combination thereof useful for joining and fastening mounting assembly 303 to floor mount 205. Other parts of floor mounting assembly 303 are similarly coupled to floor 301.

Floor 301 includes one or more penetrating holes or apertures passing through and may also appear in whole or in part as a mesh, screen, grid, or array of apertures allowing a free flow of ozone from the region beneath floor 301 (second region) to the region above it (first region). In the illustrated embodiment, floor 301 includes a generator aperture 353 coinciding with the placement of the ozone generator assembly 316 below floor 301, a converter inlet aperture 354 shown coinciding with the placement of an ozone converter inlet 340 of the ozone converter assembly 330 beneath floor 301, and a converter outlet aperture 355 through which an outlet duct 334 from the ozone converter assembly 330 passes from the second region below floor 301 to the first region above it.

In some embodiments, it may also be advantageous to limit fluid exchange between the first and second regions by fluid passing around floor 301 between the edges of floor 301 and the inside surface of inner container 200 or case 106. In these embodiments, a gasket or other sealing device may be configured around the outer edge of floor 301 or along the inner surface of container 200 and case 106 to substantially hermetically seal the edge of floor 301 to the walls of inner container 200 and case 106 thereby substantially sealing off region 1 from region 2 at the edge of floor 301.

Floor 301 may be constructed of any suitable material such as a metal or metal alloy, or of any of the polymeric materials listed above, or any combination thereof. In the illustrated embodiment, floor 301 includes sufficient rigidity to mount items such as ozone generator assembly 316 such that they may be suspended or maintained above the bottom of inner container 200. However, in other embodiments, the assemblies mounted to floor 301 may be otherwise mounted to inner container 200 and floor 301 may be a much less rigid material such as, for example, a semi-rigid sheet of metal or polymeric material having a mesh of holes or larger openings and only sufficient rigidity to maintain shape and position within inner container 200.

As shown in FIG. 3, floor 301 also includes a deflector guard 302 which is mounted to floor 301 using a deflector guard mounting fasteners 306 such as bolts, screws, pins, posts, or other such mounting device along with a deflector standoff 307 which operates to position deflector guard 302 a predetermined distance away from floor 301. Some advantages may be gained by offsetting deflector guard 302 above floor 301 such as additional airflow to ozone generator assembly 316 and ozone converter assembly 330 positioned below floor 301 while still protecting these assemblies from foreign objects that may drop downward toward floor 301. Deflector guard 302 may also include a deflector vent 308 to provide for air flow through deflector guard 302 as shown by outbound flow 323. In another embodiment, deflector guard 302 does not include vent 308, or has a vent 308 positioned in a different location relative to ozone generator assembly 316 resulting in an outbound flow 323 that passes beneath deflector guard 302 before entering the interior space around the edges of deflector guard 302 or through a vent 308 positioned elsewhere. Likewise, other embodiments of deflector standoff 307 may position deflector guard 302 further above floor 301 to provide greater opportunity for ozone enriched atmosphere to flow out of ozone generator assembly 316. Deflector guard 302 may be constructed of the same types of materials as floor 301 described above, or of other suitable materials as well. Deflector guard 302 may also be substantially the same physical size as floor 301 having a similar surface area as floor 301 thus covering approximately the same area that floor 301 does.

Ozone generator assembly 316 may be mounted to floor 301 as illustrated along with a floor support assembly 309, or may be mounted elsewhere within inner container 200 where doing so is advantageous. An ozone converter assembly 330 is also included which in the illustrated embodiment is mounted to converter assembly mount 206 shown in FIG. 2, using converter mount fasteners 344 to fasten converter mounting member 343 to converter assembly mount 206. By this arrangement, converter assembly 330 is maintained in position while floor 301 is rotated along the axis defined by floor mounting assembly 303 or removed altogether. In the illustrated embodiment where floor mounting assembly 303 includes one or hinges, ozone generator assembly 316 and floor support assembly 309 can be raised along with floor 301 by rotating floor 301 on floor mounting assembly 303 into a desired second position. This is further facilitated by a handle 305, which operates as a gripping member rigidly extending away from floor 301 for assisting in raising floor 301. Handle 305 appears in FIG. 3 as a rigid member extending away from floor 301 but may also be formed from various flexible, or semi-flexible materials which may or may not have shape memory and be resiliently deformable from a relaxed shape to a contorted, bent, or twisted shape, and able to return to their original shape when allowed to do so. In another embodiment, handle 305 includes a rigidly extending member rotatable to actuate a lock or other retention mechanism for retaining floor 301 in place.

Turning now to the separate subassemblies represented in FIG. 3, floor assembly 300 includes a floor support assembly 309 having a floor support 310 coupled to floor 301 using one or more floor support attachment fasteners 312. Floor support 310 has a support member 349 extending outwardly away from floor support 310 that is operable to contact a stop (not shown) that is either mounted to, or part of, inner container 200. Floor support 310 contacts the stop to halt the downward travel of floor assembly 300 when downward vertical force is applied to floor 301 or deflector guard 302. This downward movement can then be detected by sensing device 313 such as a roller lever snap action switch illustrated in FIG. 3 with a trigger arm 314 configured to contact a support contact arm 315 extending away from floor support 310. A biased support member 311, such as a spring, applies sufficient upward force to floor support 310 to maintain separation between floor support 310 and the previously mentioned stop, and between contact arm 315 and trigger arm 314 so that when no additional weight is placed on floor assembly 300, trigger arm 314 and support contact arm 315 do not activate sensing device 313. When an object of sufficient weight is placed on floor 301 thus overwhelming the upward biasing force of support member 311, floor support 310 moves downward until the stop is hit and support contact arm 315 also moves downward to contact trigger arm 314 closing switch 313 preferably sending a signal to a control device through leads 348 to indicate that an object within inner container 200 is resting on floor 301. Sensing device 313 is maintained in position by a mount (not shown), as is biased support member 311, both mounts being coupled to or constructed as part of inner container 200, case 106, or otherwise configured to provide rigid support.

This mechanism provides one embodiment of an entrapment warning system or foreign object detection system to warn the operator to check the chamber for foreign objects. In the preferred embodiment discussed at length below, the control device will not allow the machine to produce ozone if a foreign object is detected on floor 301, and will shut down ozone production if production is in progress and an object is detected. Examples of such foreign objects include a small child or animal that has crawled into inner container 200 unbeknownst to the operator, or an article of clothing that has come to rest on floor 301 and may be blocking deflector vent 308 (if one is provided) thus possibly obstructing the free flow of ozone enriched atmosphere from ozone generator assembly 316 into the chamber.

Floor support 310 is arranged to provide entrapment or foreign object detection by raising and lowering along the rotational path of floor 301 and, in the illustrated embodiment, physically opening or closing a roller lever snap action switch. However, other embodiments of a device responsive to objects resting on floor 301 are also envisioned. For example, light emitting devices generating infra-red, ultraviolet, laser, or other suitable devices may be used in conjunction with various suitable elctro-optical sensors or sensor arrays using devices such as photodiodes, photoconductors, photoresistors, phototransistors, charge-coupled devices (CCDs) and the like arranged and configured to detect objects resting on floor 301 or in other areas of inner container 200 where they should not be.

Ozone generation is facilitated by an ozone generator assembly 316 having an ozone generator 317. In the preferred embodiment illustrated in FIG. 3, ozone generator 317 produces ozone by corona discharge using electricity of sufficient voltage to create an arc across a spark gap. However, any suitable method of ozone generation is envisioned and other possible alternatives may include generating ozone by ultraviolet light using a vacuum ultraviolet ozone generator, or by using a cold plasma generator and pure oxygen, or by electrolytic ozone generation where water is split into hydrogen, diatomic oxygen, and ozone, or by any combination thereof.

Regardless of type, ozone generator 317 is positioned in fluid communication with the interior enclosed space defined by inner container 200. As illustrated in FIG. 3, ozone generator 317 is mounted as part of ozone generator assembly 316 beneath floor 301 within an airflow chamber 318 which has an ozone generator inlet 346 and an ozone generator outlet 347. Ozone enriched atmosphere may be pushed into the first region of inner container 200 after passing through generator 317 using an ozone generator fan assembly 319 positioned to correspond with ozone generator inlet 346.

Generator fan assembly 319 includes a fan motor 320 having rotating fan blades 321 that rotate around a central axis to create an inbound generator flow 322 into airflow chamber 318 through generator inlet 346 and a corresponding outbound generator flow 323 out of airflow chamber 318 through generator outlet 347. Thus fan assembly 319 applies positive fluid pressure to circulate the atmosphere within inner container 200 through airflow chamber 318 and past ozone generator 317 thereby decreasing the time required to achieve the desired ozone concentration. Electrical energy is provided to ozone generator 317 from a transformer 324 which operates as a voltage matching device for providing the necessary increase in voltage to generate the arcing or corona discharge used in the preferred embodiment of ozone generator 317 to create the ozone. Electric power is provided to transformer 324 through a generator power connection 325 while a separate generator fan power connection 326 provides electrical energy to rotate fan motor 320.

Other embodiments of ozone generator 317 may operate without ozone generator fan assembly 319. However, ozone generator fan assembly 319 is preferred in order to improve the performance of the overall system by decreasing the time required to reach the desired predetermined ozone concentration set point by more rapidly cycling the atmosphere within inner container 200 through airflow chamber 318. On a related note, other embodiments may find it more advantageous to position ozone generator fan assembly 319 elsewhere within inner container 200, or it may also be advantageous to place fan assembly 319 in a separate chamber in fluid communication with inner container 200.

Ozone generator assembly 316 further includes generator assembly frame 328 to which transformer 324, airflow chamber 318, and fan assembly 319 are coupled. Assembly frame 328 is then preferably coupled to floor 301 using one or more suitable generator assembly mounting fasteners 327. The ozone generator assembly 316 in the illustrated embodiment is thus coupled to floor 301 so that generator assembly 316 is suspended above the bottom of inner container 200 to allow the free flow of atmosphere into (322) airflow chamber 318, and to allow ease of maintenance as discussed above, if not for other reasons as well. However, ozone generator assembly 316 can be positioned elsewhere within inner container 200 and need not be positioned on or near the floor. Ozone generator assembly 316 can be positioned anywhere suitable for ozone production such as along the sides, top, back, or in a separate chamber in fluid communication with inner container 200 as well if preferred. In any case, ozone generator 317 is in fluid communication with inner container 200 so that an inbound flow of air 322 and outbound flow of air 323 are created to provide for the dispersal of ozone within inner container 200.

Also shown in FIG. 3 along with the other parts of floor assembly 300 coupled to floor 301 is an ozone converter assembly 330 which operates to convert the ozone to oxygen. As will be discussed in further detail below, the system includes a control device that will not allow the items placed within sanitizing device 100 to be accessed by the user until a sufficient quantity of ozone within inner container 200 has been converted to oxygen, a process that occurs naturally, but is sped along much more quickly by ozone converter assembly 330. Converter assembly 330 includes a converter housing 350 having a top 336 maintained in place by top fasteners 351. Converter housing 350 defines an interior space further divided into at least two cavities or chambers. A fan chamber 331 housing a converter fan assembly 333, and a conversion chamber 332 housing a conversion catalyst 339. Converter housing may be constructed of similar metal, metal alloys, or polymeric materials as mentioned above, and formed from one or more individual pieces using fasteners, adhesives, chemical bonding, friction fit, or any other suitable means.

Conversion chamber 332 contains a conversion catalyst 339 for decreasing the time required to convert ozone to diatomic oxygen. Ozone, under normal atmospheric conditions, will naturally decay to diatomic oxygen with a half-life of about 30 minutes. However, some materials can operate as a catalyst to increase this rate of decay. One example is a mixture of manganese dioxide and copper oxide illustrated in FIG. 3 as a loose collection of granules in conversion chamber 332. In one example, the conversion catalyst 339 are granular particles having a size of 4×8 mesh granular or about 4.8 mm by about 2.4 mm while in another example the particles are 9×14 mesh granular or about 2.4 mm by about 1.4 mm. In one embodiment, the granular particles of catalyst 339 have a surface area of approximately 200 $m^2/g$. One embodiment of conversion catalyst 339 having some or all of these properties is CARULITE® 200 which is commercially available from the Carus Corporation, of Peru, Ill., USA.

To further speed along the conversion process, fan chamber 331 contains a converter fan assembly 333 having a converter fan motor 337 which operates to rotate converter fan blades 338. In the preferred embodiment, converter fan motors 337 uses electricity provided by converter fan power leads 345 to rotate converter fan blades 338 moving air through fan chamber 331 from a converter inlet 340 to converter outlet 352. This movement of air causes a converter inbound airflow 341 to occur where air moves from within inner container 200 through a converter inlet 340 into conversion chamber 332. The ozone enriched air passes through conversion catalyst 339 causing an increase in the rate of conversion from ozone to diatomic oxygen as it passes through the conversion catalyst 339. Air is then pushed through converter fan assembly 333 and out of converter housing 350 through converter outlet 352 which has an outlet duct 334 coupled to converter housing 350 using outlet duct fasteners 335. Thus converter fan assembly 333 creates fluid circulation of the atmosphere within inner container 200 through ozone converter assembly 330. Converter inbound flow 341 enters ozone converter assembly 330 and leaves as converter outbound flow 342 somewhat ozone depleted. The rate of the conversion process can thus be controlled in large part by a controller (discussed below) connected to fan power leads 345 which can start and stop the convert fan motor 337 to increase or decrease the rate of conversion of ozone to diatomic oxygen.

As with ozone generator assembly 316, ozone converter assembly 330 may not be present within inner container 200 in other embodiments, but may be positioned in a separate chamber that is in fluid communication with inner container 200. Likewise, ozone converter assembly 330 need not be positioned in the lower regions of inner container 200 and may be positioned elsewhere such as on the top, sides, back, or anywhere else. Positioning ozone converter assembly 330 in the lower regions of inner container 200 may be advantageous for various reasons, one of which being that its efficiency may be enhanced due to the fact that ozone is heavier than air and will thus naturally tend to be in richer concentrations near the floor of inner container 200. In other embodiments, no ozone converter assembly is present, relying instead on the natural breakdown of ozone to oxygen which occurs without any conversion process.

Figure 4:
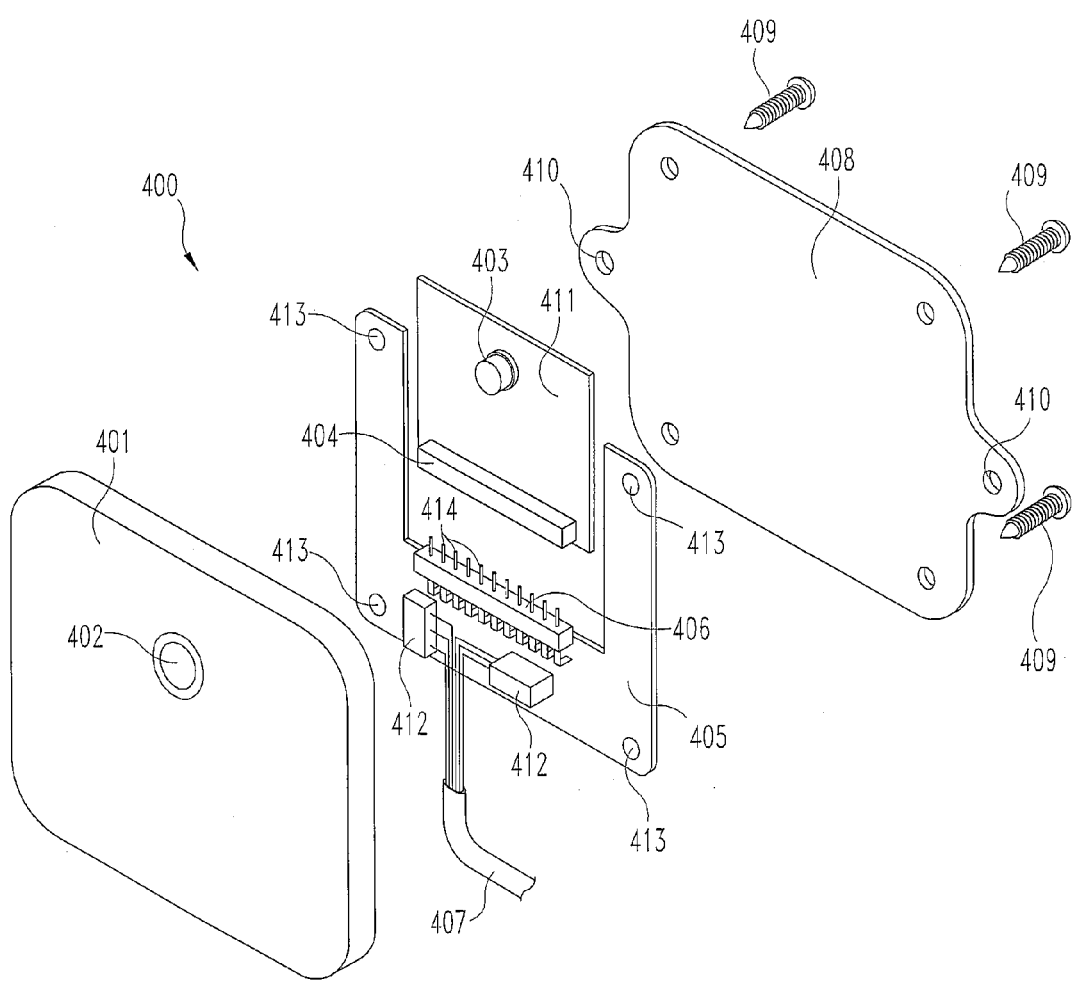
FIG. 4 is an exploded perspective view of one embodiment of a sensor assembly from FIG. 2.

In order for ozone sanitizing system 100 to properly control the concentration of ozone within inner container 200, a sensing device is helpful in creating a feedback loop between the sensing device, a controller (discussed below), and the ozone generator assembly 316 and converter assembly 330. In FIG. 4 is shown an exploded perspective view of one embodiment of a sensor assembly 400 in fluid communication with inner container 200 and operable to sense various aspects of the current atmospheric state within inner container 200 such as the current temperature, humidity, and ozone concentration. Sensor assembly 400 includes a front cover 401 having a sensor aperture 402 providing fluid access to a sensing device 403 that is operable to measure one or more current state properties of the atmosphere such as temperature, humidity, ozone concentration, and the like. Sensor module 411 also includes a sensor module connector 404 for coupling the sensor module 411 to a sensor control board 405 having sensor control circuitry 412 for collecting sensor readings from sensing device 403 and converting them into a data stream for electronic devices coupled to one or more sensor leads 407.

Sensor module 411 is preferably coupled to sensor control circuitry 412 by coupling sensor module connector 404 to a control board connector 406 using a pluggable connector where connectors 404 and 406 can be non-destructively connected and disconnected by inserting some part of one of the connectors into the other. In one embodiment, control board connector 406 has one or more pins 414 projecting outwardly from control board connector 406 which are configured to correspond to a series of receptacles in sensor module connector 404 such that the pins can be inserted into the receptacles without damaging the connectors. However, other embodiments are envisioned where pins 414 may project from connector 404 with corresponding receptacles on connector 406, or different types of connectors 404 and 406 may be used that do not employ projecting pins but one or more contacting members maintained in contact by a plug inserted within a receptacle and retained in position by a snap, any sort of suitable fasteners, friction, or other suitable retention means. Regardless of the embodiment used, this pluggable arrangement is advantageous to reduce maintenance time and cost by requiring only sensor module 411 to be replaced when sensing device 403 becomes inoperable. This can be executed by unplugging sensor module 411 and replacing it without replacing all of sensor assembly 400, and without having to destructively remove sensing device 403 at the risk of destroying other parts of sensor assembly 400.

Sensor assembly 400 has a rear cover 408 coupled to a front cover 401 using sensor assembly fasteners 409 which pass through control board mounting holes 413 and fasten to front cover 401. Sensor assembly mount 410 extends outwardly from rear cover 408 and provides a means for mounting sensor assembly 400 to inner container 200. Sensor assembly 400 need not be mounted as shown in FIG. 2 rather it can be mounted to the top, bottom, or side, or anywhere in fluid communication with inner container 200 where sufficiently reliable atmospheric measurements can be taken. For example, in another embodiment, ozone sensor assembly 400 may be in a separate chamber or container in fluid communication with inner container 200, or in a separate compartment within inner container 200.

Figure 5:
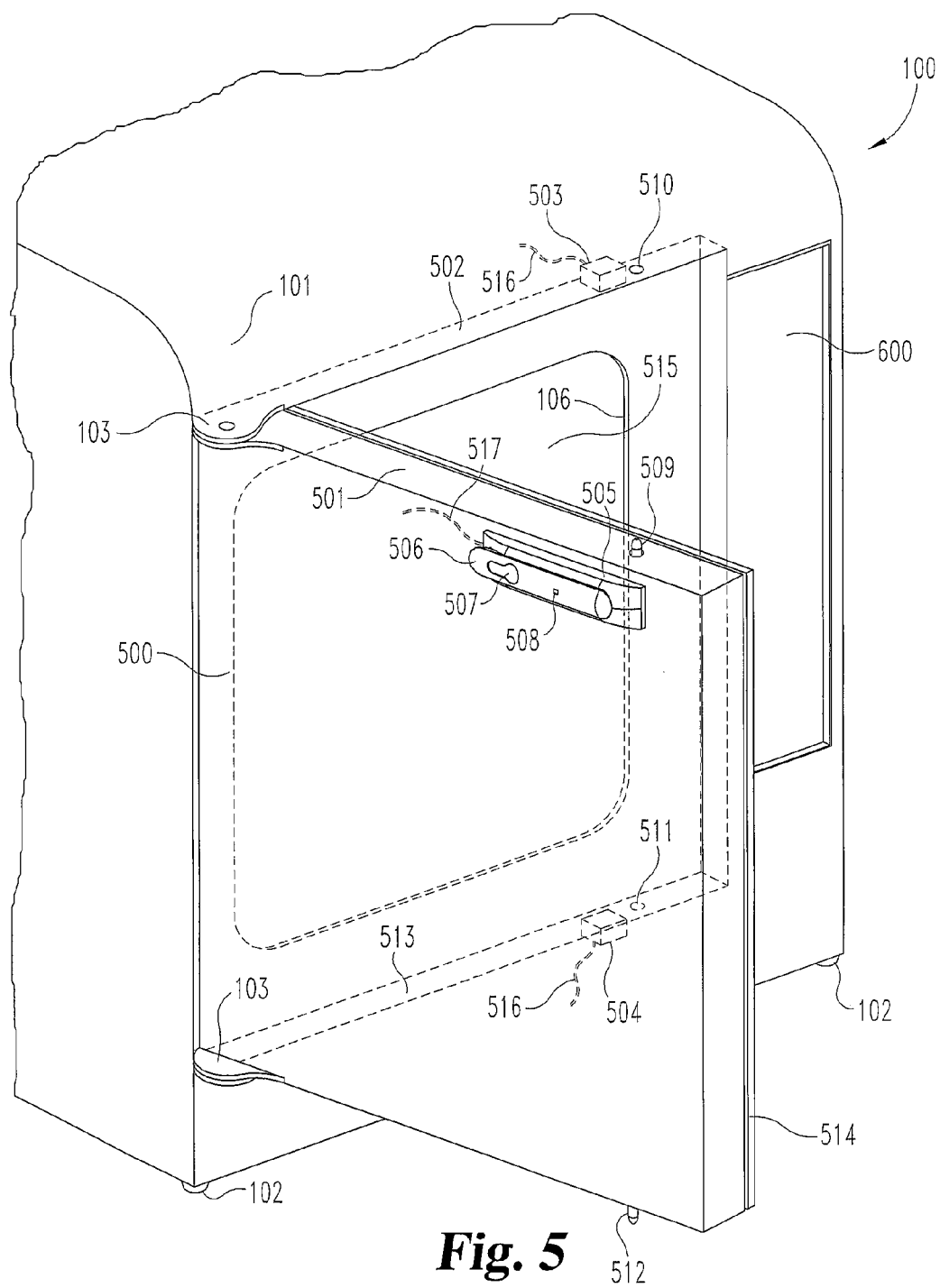
FIG. 5 is a perspective view showing further detail of the embodiment from FIG. 1.

In order for sanitizing device to maintain the proper ozone concentrations, a door or other selectively closeable opening is positioned over the opening in inner container 200 and case 106. FIG. 5 shows one embodiment of door assembly 500 having a door 501 illustrated in the open position. A door 501 operates as a selectively closeable opening for covering an opening 515 defined by case 106 which provides access into the enclosed space defined by inner closure 200. Case 106 also provides a sealing contact surface for a door seal 514 which is coupled to the inside surface of door 501. Door seal 514 may include any sort of gasket or similar sealing device constructed of rubber, plastics or other polymeric materials, or any other suitable substances.

When door 501 is in the closed position (as shown in FIG. 1) seal 514 operates as a gasket or sealing member to substantially hermetically seal door opening 515 to case 106 so that ozone released within the enclosed space of inner closure 200 is maintained within inner closure 200 allowing no substantial quantities of ozone to escape. As discussed above with reference to the embodiments illustrated in FIG. 2, inner container 200 also maintains a sealed relationship with the opposite side of case 106 using a similar gasket or sealing member 204, and is designed and assembled with the goal of allowing no ozone to escape. Therefore, when door 501 is closed, a substantially hermetically sealed environment is created inside inner container 200 to contain the ozone enriched atmosphere to avoid the risk of harm to the operator or others nearby. In other embodiments, case 106 may not be positioned between door 501 and inner container 200 and in such an arrangement, seal 514 contacts inner container 200 directly to form a hermetic seal. Various other similar arrangements of a door or closure to enclose and seal an opening in inner container 200 are envisioned as well.

Door assembly 500 is maintained in position by an upper doorframe 502, and a lower doorframe 513 to which are mounted hinges 103 for rotatably mounting door 501 to cabinet 101. Also included with door assembly 500 are an upper sensor 503, and a lower sensor 504 positioned to interact with door 501 to determine when door 501 is closed or open, and to relay that information to a control circuit (discussed in detail below) via sensor leads 516. One embodiment of upper and lower sensors 503 and 504 is a snap action switch that is physically actuated to open an electric circuit when door 501 is open, or actuated to close an electric circuit when door 501 is closed. Another embodiment of upper and lower sensors 503 and 504 is a magnetic reed sensor proximity switch which detects the nearby presence of magnets and magnetic fields such as the model MP2018 magnetic reed sensor commercially available from the ZF Electronics Corporation of Pleasant Prairie, Wis., USA. These are but examples of a wide variety of suitable sensor devices envisioned for determining when door 501 is open or closed.

Door 501 is also maintained in position by an electronic lock assembly 505 responsive to a controller through lock leads 517 which can carry signals indicating both the current state of the lock mechanism (e.g. "locked" or "unlocked") to the controller while also receiving signals from the controller to actuate the lock. Lock assembly 505 also includes a handle 506 for manipulating upper locking pin 509 and a lower locking pin 512 between locked and unlocked positions. In one embodiment, outwardly extendable handle 506 may be actuated, such as by rotating handle 506, to move locking pins 509 and 512 into the locked position thus making it possible for the controller to initiate a "lock" signal to the electronic lock assembly 505 to lock door 501 and secure it into place. In the locked position (as shown in FIG. 5) upper locking pin 509 protrudes into upper lock receiving hole 510, and lower locking pin 512 likewise protrudes into lower lock receiving hole 511.

Lock assembly 505 preferably includes a manual override 507 such as a mechanism for accepting and turning a key, one or more buttons or levers, or any other suitable device for manually overriding electronic lock assembly 505. This procedure may be necessary in some situations such as during a power failure when lock assembly 505 becomes unresponsive due to a loss of power. When power is lost during a sanitizing cycle, lock assembly 505 preferably remains locked to avoid exposing the operators to potentially high concentrations of ozone contained inside the device. Because ozone has a half life of about 30 minutes and will therefore naturally reduce its concentration to a safe level with the passage of time, the operator need only wait for a safe period of time to pass before overriding the electronic lock mechanism by actuating the manual override 507 to unlock lock assembly 505 and release the door 501.

Lock assembly 505 also preferably includes a lock indicator 508 indicating when the electronic lock assembly 505 is locked or unlocked. The indicator 508 may also be located elsewhere such as on door 501, or control panel 600 (discussed in more detail below). Lock indicator 508 is preferably a light or LED or other electronic device responsive to the electronic locking mechanism or to a control circuit that is able to indicate the states lock assembly 505 is in such as "locked", "unlocked", and others if applicable. However, any suitable indicia is envisioned as well such as toggles, sliding or rotating indicators, or more complex examples such as LED or LCD displays. The indicator may also change colors when the lock moves from the locked to the unlocked state, or may switch from an "on" or "lit" state to an "off" or "unlit" state.

Figure 6:
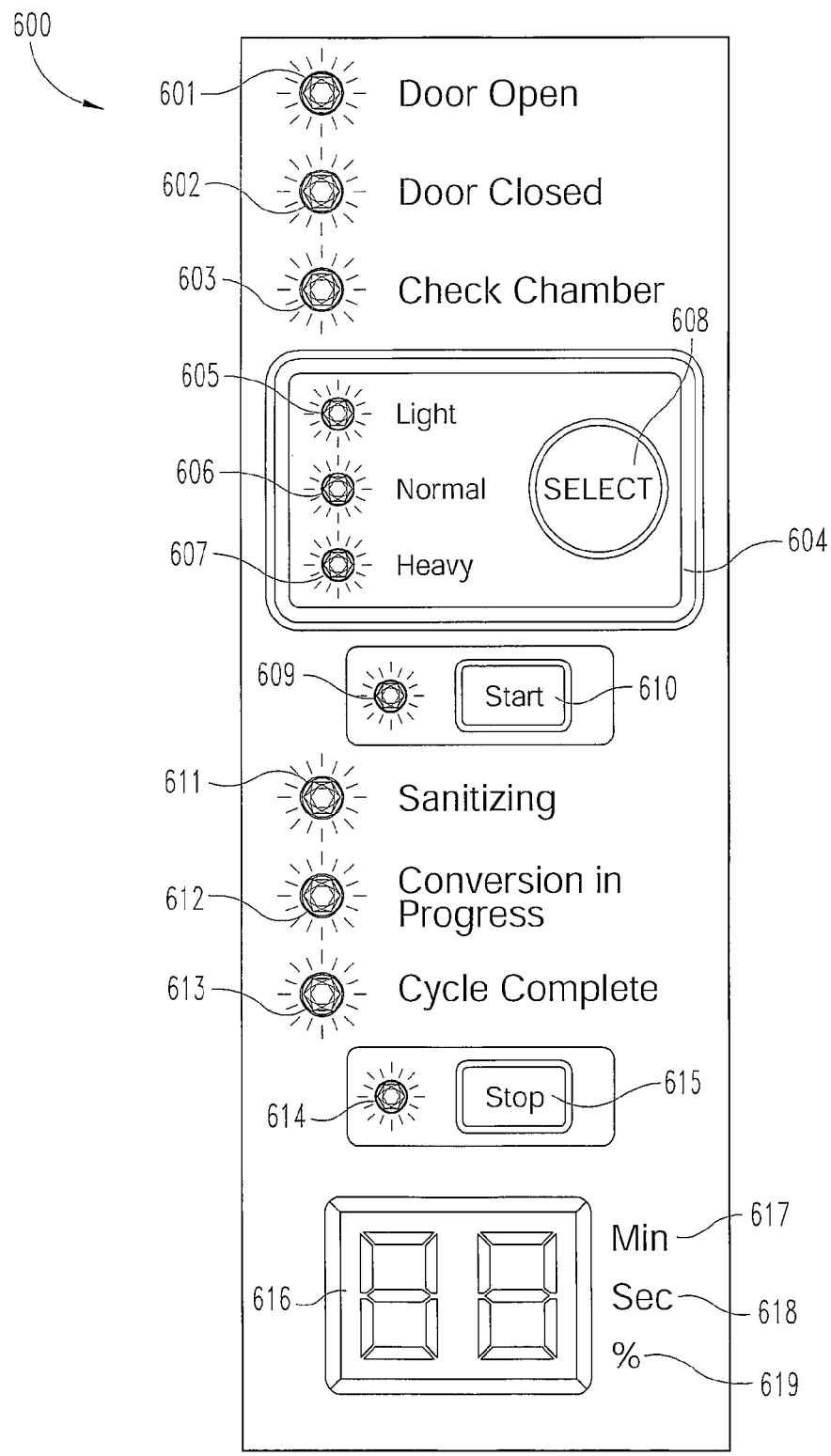
FIG. 6 is a diagrammatic view of one embodiment of a control panel included in the device of FIG. 1.

Turning now to control aspects of sanitizing system 100, a diagram of one embodiment of a control panel 600 is shown in FIG. 6. Control panel 600 includes a door open indicator 601 to indicate when the door is open, and a door closed indicator 602 indicating when the door is closed. Preferably, indicators 601 and 602 would not be activated at the same time. Control panel 600 also includes an entrapment or check chamber indicator 603 which is activated when a foreign object sensing device such as sensing device 313 shown in FIG. 3 indicates a foreign object is present inside inner container 200. As discussed above, this can occur in various ways, such as by detecting the downward movement of floor 301 caused by the weight of an object placed on floor 301 of floor assembly 300.

Control panel 600 also includes a cycle selection panel 604 having a cycle selector 608. Cycle selection panel 604 also includes a light cycle selection indicator 605, a normal cycle selection indicator 606, and a heavy cycle selection indicator 607. Manipulating the cycle selector 608 activates indicators 605, 606, and 607 in turn such that in the preferred embodiment, only one of indicators 605, 606, or 607 is active at a time indicating that only one cycle can preferably be selected at a time. Further included in control panel 600 is a start selector 610 for starting a sanitizing cycle having a start selected indicator 609 to indicate when the start selector has been pressed or otherwise manipulated. A stop selector 615 is also included along with a stop selected indicator 614 to indicate when the stop selector has been manipulated as well. In one embodiment, manipulating the start selector begins the sanitizing cycle selected using selector 608, or in another embodiment, manipulating the start selector starts whatever cycle was previously completed.

Control panel 600 in the illustrated embodiment also includes a status indicator, or set of indicators, such as an "ozone generation" indicator 611, a "conversion in progress" indicator 612, and a "cycle complete" indicator 613. Along with these, control panel 600 includes a multifunction display 616 embodied in FIG. 6 as two seven segment LED displays. Multifunction display 616 includes status or stage indicators 617, 618, and 619 to provide further meaning to the information shown in multifunction display 616. A "minutes" indicator 617 indicates that minutes are remaining in the sanitizing cycle and therefore the numbers in multifunction display 616 indicate minutes remaining. A "seconds" indicator 618 indicates that seconds are remaining in the sanitizing cycle and that seconds appear on display 616. As the "soak" or "sanitize" phase of the sanitizing cycle finishes, and the "conversion" phase begins, the percentage of ozone remaining in the atmosphere inside interior container 200 appears in the multifunction display 616 and a percent of ozone remaining indicator 619 is activated. Preferably only one of indicators 617, 618, and 619 are active at any one time. These indicators may appear group together differently, or appear in other embodiments such as a single LCD, LED, or other screen or readout with alphanumeric characters indicating the progress of the remaining phase on the display. In another embodiment, control panel 600 may be a touch screen LCD or LED programmed to display the indicators or controls discussed above as graphical symbols, icons, static or animated figures, graphs, dials, or other suitable display elements useful for controlling the sanitizing system 100. In other embodiments, the indicators above may also be any sort of light, LED, or other electric or electronic indicating device. Likewise, the selectors mentioned may be any suitable button or series of buttons, knob, encoding wheel, and the like. Control panel 600 also includes one embodiment of labeling used along with the various indicators and selectors that is exemplary and may vary depending on position of the elements in control panel 600, spacing, and the particular elements included.

Figure 7:
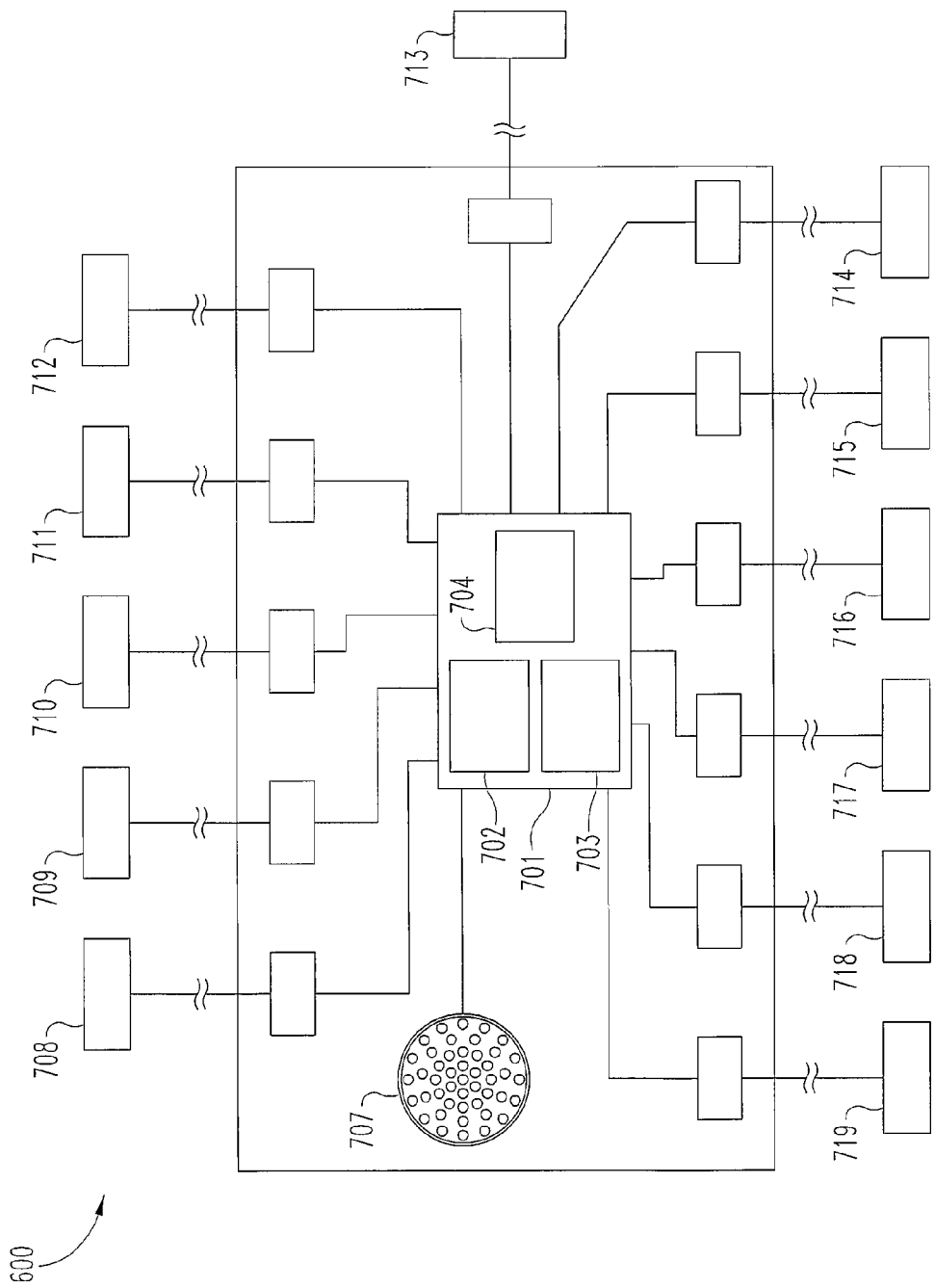
FIG. 7 is a block diagram of one embodiment of the controller included in the device of FIG. 1.

Further considering the control aspects of sanitizing device 100, one embodiment of a controller 700 is illustrated in FIG. 7. Controller 700 includes control logic for operating sanitizing device 100 taking input from the various components discussed thus far, and possibly others, and coordinating their successful operation. As shown in FIG. 7, controller 700 includes a controller circuit 701 which includes a logic circuit 702 for controlling various devices based on inputs received, a timer circuit 703 managing time, and a memory 704 for maintaining operating parameters, recently taken measurements from sensors such as ozone sensor 403, as well as maintenance service parameters useful for maintaining and operating a sanitizing system 100. Control circuit 701 can manage control signals and electrical power feeding through the system as well. Electricity from power switch 105 (see FIG. 1) connects to controller 700 and control circuit 701 at 716. Controller 700 can then be configured to control power to various system components as determined by logic circuit 702. Some embodiments of controller circuit 701 may include logic circuit 702, memory 704, and timer circuit 703 in a single miniature semi-conductor circuit packaged in a single integrated circuit package. One example of such an embodiment of control circuit 701 is PIC18F46K22 microcontroller commercially available from Microchip Technology Inc., Chandler, Ariz., USA. However, other embodiments of controller circuit 701 may use separate integrated circuits packages for circuits 702, 703, and 704, while in still other embodiments, circuits 702, 703, and 704 may be implemented using circuits and electronic components not packaged in integrated circuit packages (e.g. arrangement of independently packaged diodes, transistors, resistors, capacitors, and other similar electronic components). On a related note, memory 704 preferably includes nonvolatile memory circuits that are able to maintain stored data even if power to memory 704 is interrupted. Exemplary embodiments of such circuits include Erasable Programmable Read Only Memory (EPROM), Electrically Erasable Programmable Read-Only Memory (EEPROM), flash memory, Ferroelectric Random Access Memory (FRAM), or Magnetoresistive Random Access Memory (MRAM).

Controller 700 is responsive to various sensors such as a temperature sensor coupled to controller 700 at 710, a humidity sensor coupled at 711, and an ozone sensor coupled to controller 700 at 709. In some embodiments of the system, these three sensor inputs may be combined into a single connection point having one electrical connector connecting temperature, humidity, and ozone sensing signals to controller 700 with one physical connector. Similarly controller 700 is responsive to an entrapment or foreign object sensor such as sensing device 313 connected at 718 and door position sensor such as upper and lower sensors 503 and 504 connected at 719 where either one or both connectors may be connected depending the desired implementation.

As noted above, controller 700 also generates control signals or manages power to various components in the system. A connection to the ozone generator 714 is maintained in order to activate and deactivate the ozone generator such as by controlling power to generator power connection 325 and allowing power to flow to transformer 324 when ozone production is required. At about the same time, power may be varied to ozone generator fan power connection 326 through electrical connection 715 maintained in order to command the ozone generator fan to start, stop, or change speed. Likewise, an electrical connection to the ozone converter fan power leads 345 is also preferably maintained at 713 so that controller 700 can adjust the ozone conversion rate by starting and stopping the flow of atmosphere through the ozone converter. Similarly, a connection to the electronic lock assembly 505 is also maintained at 717 so that controller 700 may send signals to lock and unlock the electronic door lock assembly 505. Controller 700 also has an electrical connection to a beeper 707 which operates as an auditory warning device which can be activated to emit steady or pulsing tones of various pitches or volumes in situations where an audible warning is warranted.

Also connected to controller 700 is a maintenance port 708 which allows a maintenance device connection to be made through maintenance port 104 to couple the maintenance device to controller 700, logic circuits 701, and memory 704. Using this connection, information such as operating and system parameters as well as data regarding the current state of the atmosphere within inner container 200 can be passed back and forth between the maintenance device and controller 700. Also, changes to the operating logic used by logic circuit 702 may also be made via maintenance device connection 708. Likewise a connection 712 is maintained between controller 700 and control panel 600 allowing the user to control the device by making various selections as described above such as sanitizing cycle, start, stop, and other operating parameters. In all cases, FIG. 7 is illustrative in that some, none, or all of the electrical connections shown are representative and do not indicate a specific connection location relative to another location, nor do they indicate a specific number of wires connected in any case.

FIGS. 8 to 12 are flow charts which collectively illustrate one embodiment of the logical flow controller 700 executes in the control of the various components of sanitizing system 100. Beginning with FIG. 8, the system is operable when it reaches ready state 800. Ready state 800 is preferably achieved after power is applied (801) and the system performs a self test (802). The self test procedure may include steps such as activating and deactivating various indicators such as 601, 602, 603 and others on control panel 600; actuating electronic lock assembly 505 from a locked to an unlocked state; and possibly activating sensing device 403 and testing for an appropriate range of temperature, ozone, humidity, or other atmospheric sensor readings to determine if they are within reasonable ranges. These and various other types of activities like them may be included in the self test (802) procedure to determine if sanitizing system 100 is ready to operate.

Figure 8:
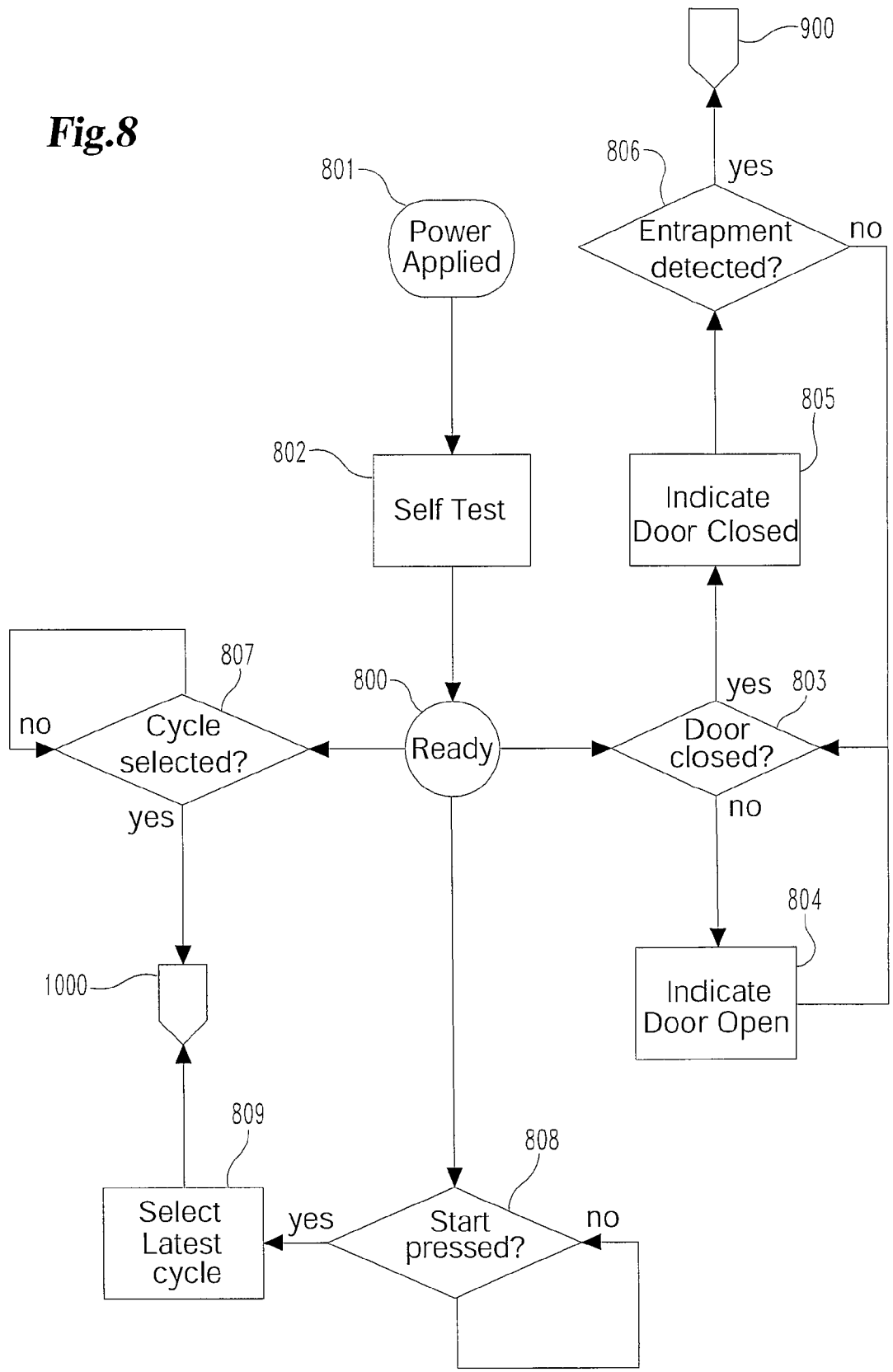
FIGS. 8-12 are flow charts indicating the logical flow of operations executed by one embodiment of the controller of FIG. 7.
Figure 9:
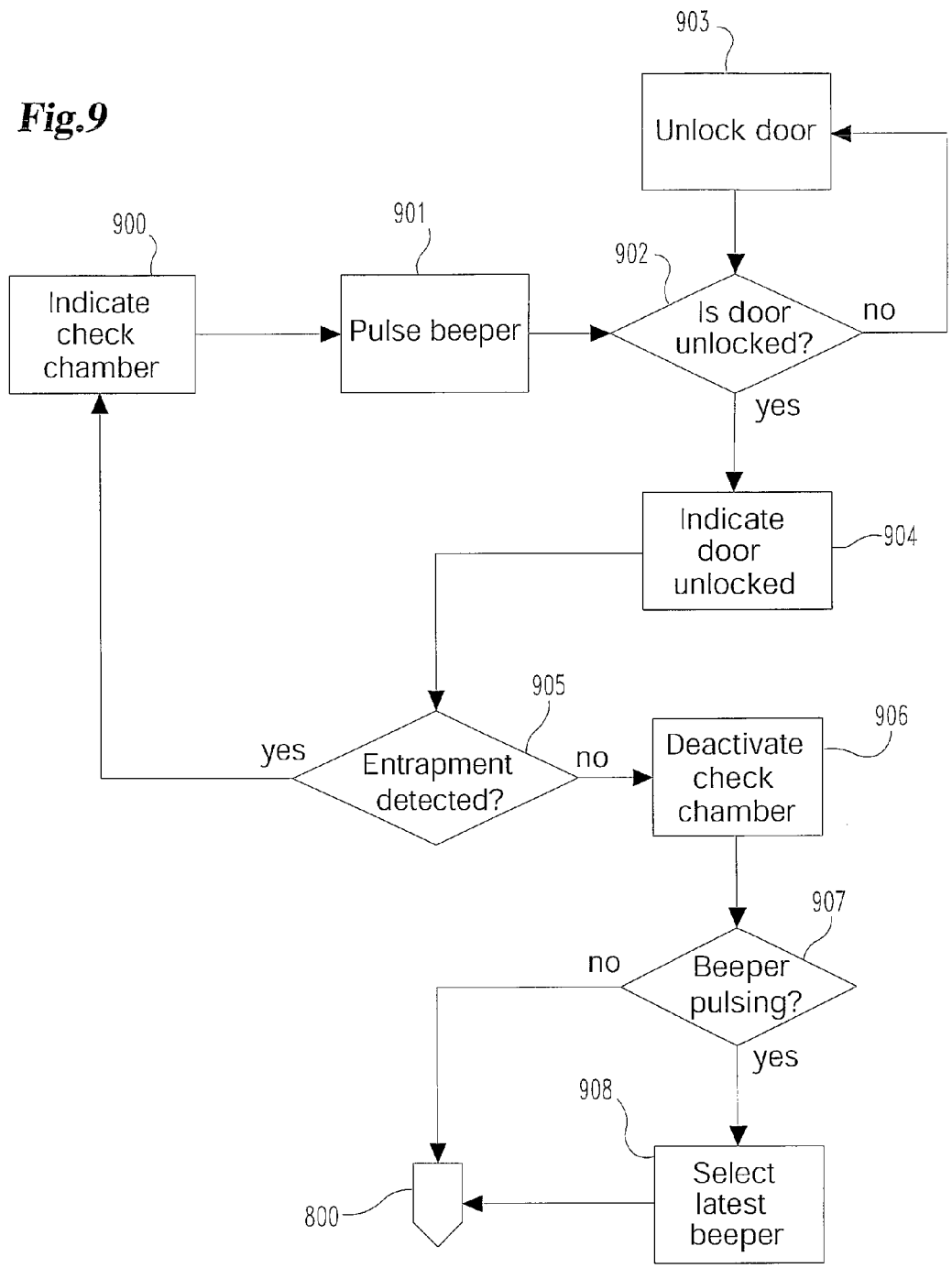
Figure 10:
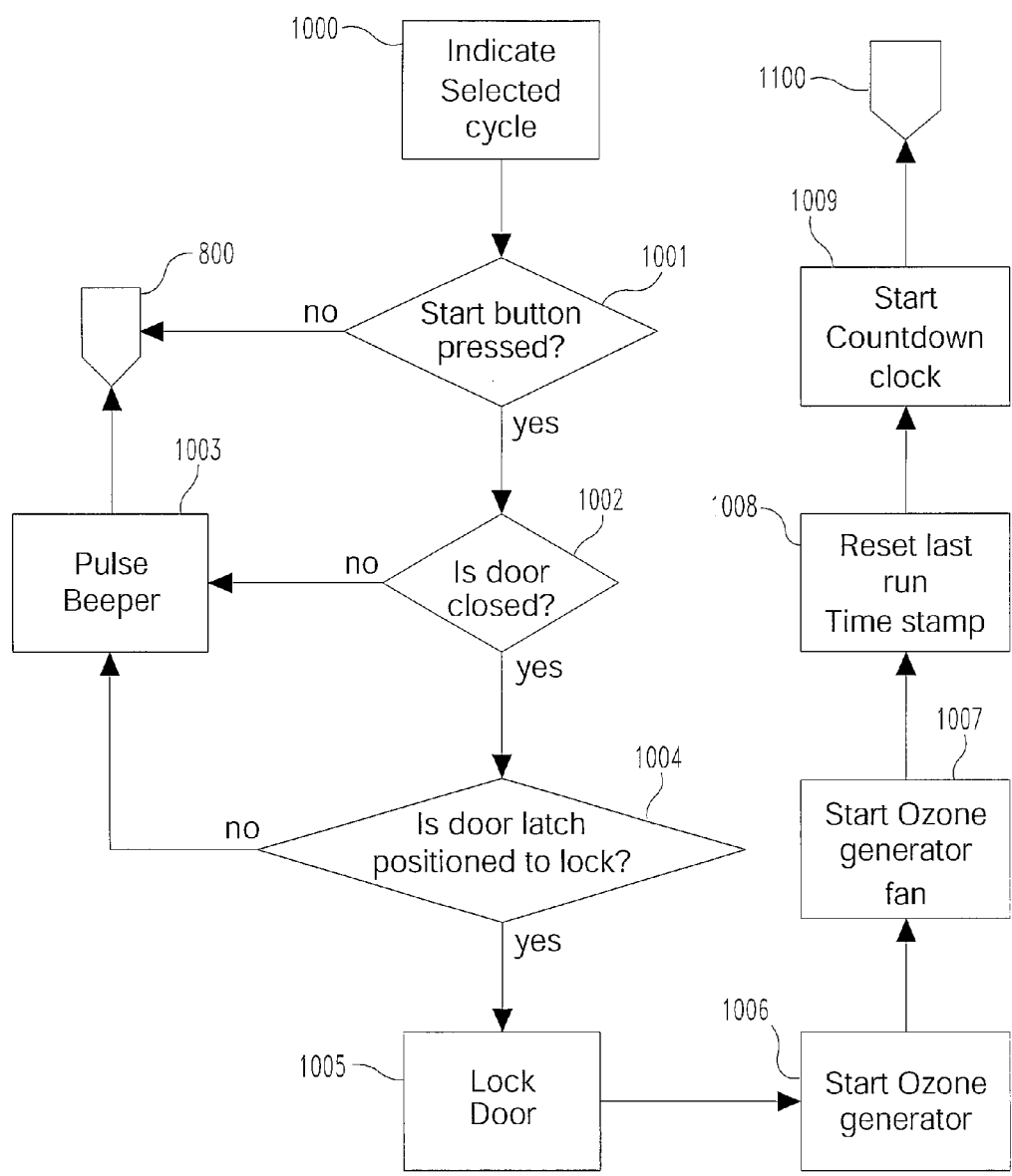

When the system is ready to begin operations (800), various activities may be engaged in at any time as indicated by multiple arrows leaving that particular step, such as, for example, ready step 800. This is intended to indicate that various logical paths of execution are, or may be, handled simultaneously in an asynchronous fashion. As illustrated in FIG. 8, selecting a cycle (807), closing the door (803), and pressing the start button (808) are operations that the user may engage in at any time when the system is red (800) and not necessarily in a predetermined order. Therefore controller 700 manages these activities asynchronously so that the system can respond to any one of them at essentially any time.

For example, when the ready state (800) is reached, part of the logical operation includes monitoring the position of the door (803). If the door is closed, the system indicates the door is closed (805) such as by activating a "door closed" indicator on the control panel (for example indicator 602). If an entrapment is detected (806) then processing continues with the entrapment detection logic at 900 shown in FIG. 9. If no entrapment is detected (806), then the system returns to checking whether the door is closed (803) and the logic repeats execution. In this way, the door close indicator and the entrapment detection sequence are activated when the door is closed and not when it is open. If the door is not closed (803) an "door open" indicator is activated where it is available (such as door open indicator 601 on control panel 600). In this case, the entrapment detection loop is not engaged and control returns back to step 803 so that when the door is closed proper indication can occur and the entrapment detection cycle can begin again as necessary.

As noted above, when the door is closed, it is advantageous to begin an entrapment detection sequence as well to determine if people, animals, or other foreign objects entered the chamber without the operator's knowledge, or were inadvertently positioned to block the flow of ozone. The entrapment detection logic is detailed in FIG. 9 where a "check chamber" indicator is activated (900), preferably on a control panel or other area where it will be readily visible. It is also preferable to pulse a beeper or buzzer (such as beeper 707) or other auditory signal (901) as well in order to obtain the attention of the operator. If the door is not unlocked (902), then the controller will activate the door lock to unlock the door (903) and send a signal that the door is unlocked (904). If entrapment is still detected (905), then the loop is repeated at step 900. This logical loop will continue as long as entrapment detection occurs. However, when entrapment is no longer detected (905), the check chamber indicator activated in step 900 is deactivated (906) and if the beeper is still pulsing (907) then it is deactivated (908) and logical processing continues at the ready stage (800).

Regardless of whether the doors are open or closed, the user can select a cycle. When a cycle is selected (807) from the ready state (800), the logical steps involved in executing a cycle begin that with the indication of the selected cycle (1000) on FIG. 10. Similarly if start is pressed (808) the last cycle selected is again selected (809) and operations continue at step 1000 and FIG. 10 as well. When a cycle has been selected, the selected cycle is indicated (1000) and the system remains in the ready state (800) until the start button is pressed. When the start button is pressed (1001), the system checks to see if the doors closed (1002). In the preferred embodiment, ozone generation cannot proceed if the door is open. Therefore if the door is not closed (1002), the system pulses the beeper for a predetermined length of time (such as 5 seconds) to warn the operator that the door is open and then returns the system to the ready state (800). If the start button is pressed (1001) and the door is closed (1002), the system checks to determine if the door latch can be locked (1004). If not, the beeper is pulsed again (1003) for a predetermined time period (such as 5 seconds) and the system returns to the ready state (800). When the start button is pressed (1001) after the door is closed (1002) and the door latch is positioned to lock (1004), the door is locked (1005) and ozone generation begins. The ozone generator is started (1006), the ozone generator fan is started (1007), the system resets the last run time stamp system parameter (1008), and a countdown clock is started (1009).

Figure 11:
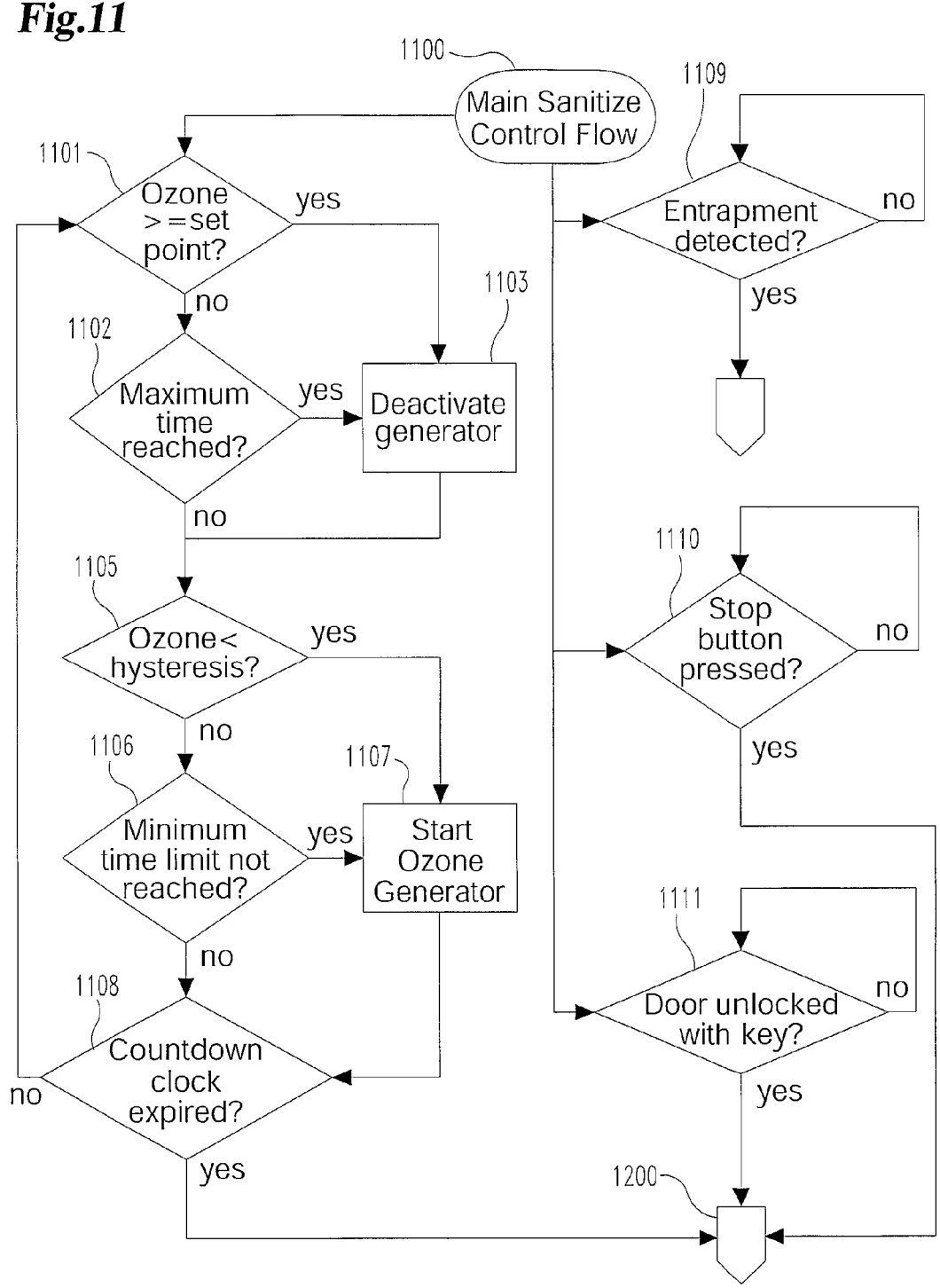
Figure 12:
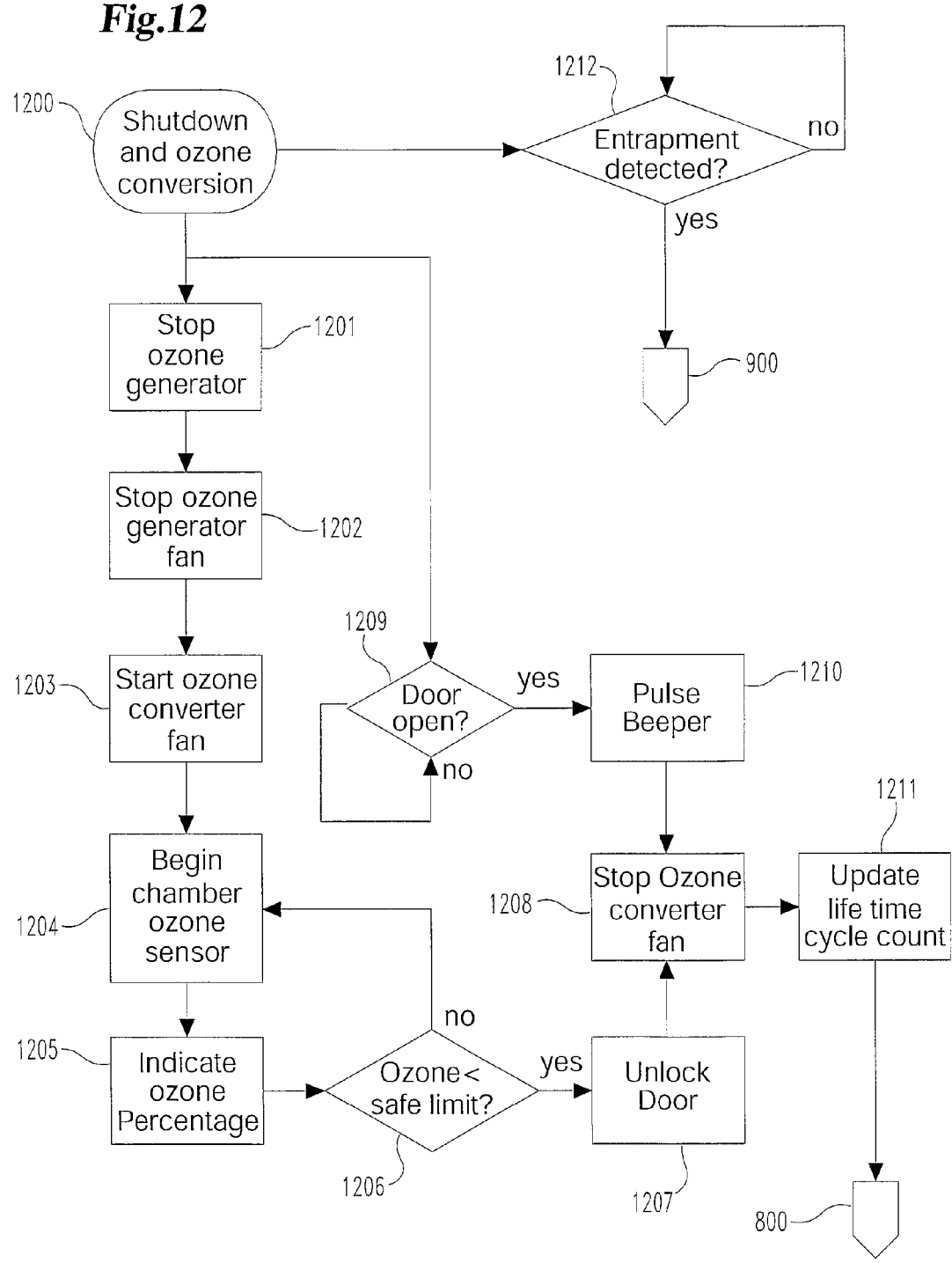

Having begun ozone generation, the system now enters the main sanitization control loops which are illustrated in FIG. 11. Here, as in FIG. 8, several control operations occur asynchronously or simultaneously in the preferred embodiment. In the main control loop the ozone sensor is monitored to determine if the ozone concentration within the inner chamber is greater than or equal to a predetermined setpoint (1101). If the concentration exceeds the setpoint, then the ozone generator is stopped (1103). If the setpoint has not been reached (1101), then the system determines whether a maximum predetermined time limit has been reached (1102). This time limit (1102) can be determined by experimentation and avoids failures that may arise when the ozone generating equipment has operated for too long at any one time, as well as an upper limit on the ozone concentration inside cabinet 101. If the maximum time is reached (1102), ozone generation stops (1103) and processing continues. At this point the ozone generator may still be generating ozone or it may have been shut down if ozone saturation has reached a predetermined setpoint or the maximum time has been reached for ozone generation to occur.

If the ozone is less than a predetermined setpoint (1101, 1102), then the controller checks to determine if the ozone concentration is less than a stored hysteresis value (1105). The stored hysteresis value allows the current ozone concentration within the enclosed space to deviate from the predetermined setpoint by a predetermined range. Adjusting the hysteresis value allows the predetermined range to be expanded or narrowed. This serves, among other things, to reduce the number of times the ozone generator is started and stopped as the ozone concentration deviates from the predetermined setpoint. If the ozone concentration is less than the hysteresis value, then ozone generation is started (1107) and the controller checks the countdown clock for expiration (1108). If ozone concentration is not less than the hysteresis (1105), then the controller determines whether a minimum time limit for ozone generation has not been reached (1106) and if not, ozone generation starts (1107) if it is not already occurring. The predetermined minimum time limit operates to avoid situations such as a faulty ozone sensor reading a high concentration of ozone when no such concentration exists within the chamber thus causing the ozone generator to create an insufficient quantity of ozone to perform the proper sanitizing operation. If the minimum time limit has been reached, then the control loop described repeats itself until the countdown clock expires (1108) and the shutdown and conversion process begins at step 1200.

While the sanitizing control loop is processing and ozone is being generated to maintain the proper saturation for the proper length of time, the controller also monitors for entrapment detection (1109) and executes the entrapment detection procedures discussed previously with respect to FIG. 9 if detected within the chamber (900). The Main sanitizing control flow can also be halted or preempted by pressing the stop button (1110) or by unlocking the door with the key (1111). In either of these cases, as with the expiration of the countdown clock (1108), processing continues with the shutdown and conversion steps illustrated in FIG. 12.

Shutdown and ozone conversion (1200) includes stopping ozone generation (1201) stopping the ozone generator fan (1202), starting the ozone converter fan (1203) and beginning a feedback loop on the ozone sensor by reading the ozone sensor (1204), indicating the ozone concentration (1205) within the chamber, and continuing this monitoring loop as long as the ozone concentration is greater than a predetermined safe limit (1206). When the ozone concentration is reduced to a concentration less than or equal to a safe limit, the controller unlocks the door (1207) stops the ozone converter fan (1208), and the system is once again ready (800) to begin another sanitizing cycle.

As with previous logical illustrations, if entrapment is detected (1211), the entrapment detection routines are processed (900). Similarly, if during the shutdown and ozone conversion process the door is opened (1209), the beeper is activated, for example by pulsing it (1210), the ozone converter fan is stopped (1208), and the system is ready (800) to begin another cycle.

Figure 13:
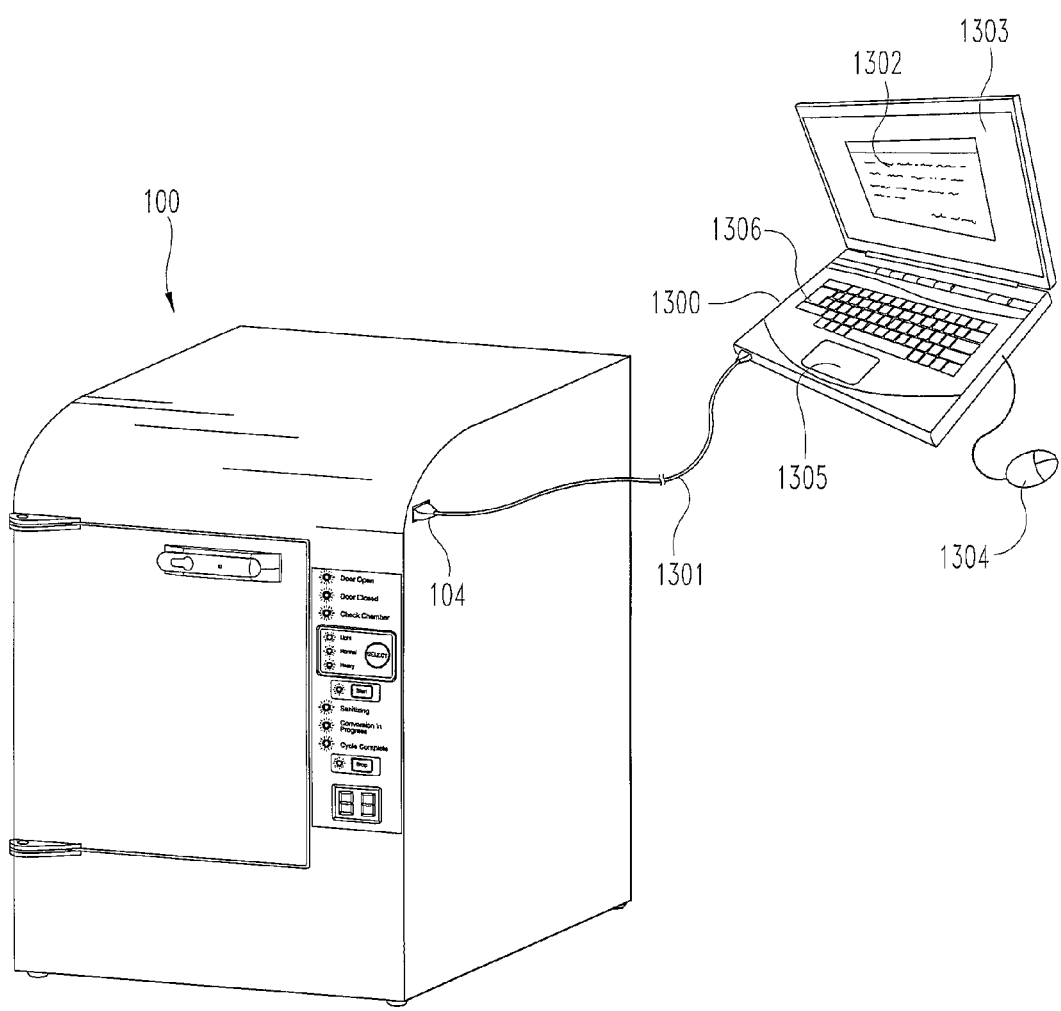
FIG. 13 is a perspective view of the device of FIG. 1 coupled to one embodiment of a maintenance device.

FIG. 13 illustrates another aspect of sanitizing system 100 whereby a maintenance device 1300 is connected to sanitizing system 100 in order to change operating parameters, system parameters, and to access data or information such as recent atmospheric measurements within the chamber collected during sanitizing operations. As shown in FIG. 13, a maintenance device coupling 1301 such as a cord or other suitable device is coupled to connection port 104 into maintenance device 1300. Embodiments of device coupling 1301 include a cord such as a USB cord, IEEE 1394 cable (also known as FireWire®, or i.Link®) or other similar cable. The connection may also be made wirelessly using a combination of radio transmitter and receiver and the like as well such as by installing wireless networking transmitting and receiving equipment in sanitizing system 100 to allow it to communicate with maintenance device 1300 without cables.

Maintenance device 1300 may be a custom-made device specifically designed to access system parameters, operating parameters, and recent measurements made by the sensors within sanitizing system 100 as it is operating. Or maintenance device may be a general purpose computer or other suitable personal computing device. In either case, or in others, maintenance device 1300 includes one or more display devices 1303 using Liquid Crystal Display (LCD), Light Emitting Diode (LED), plasma, Cathode Ray Tube (CRT), or any other suitable display technology for displaying data and information generated from data provided by sanitizing system 100 through device coupling 1301. Maintenance device 1300 may also include one or more various input devices such as a keyboard input device 1306, a touch pad input device 1305, or a mouse input device 1304, or a touch-screen input device 1303 where display device 1303 is responsive to the touch of the user or of an object such as a stylus or a pen. Maintenance device 1300 also includes one or more logic circuits which may be packaged in one or more integrated circuit packages or processors executing maintenance software 1302 to display the parameters and sensor data collected from sensors in sanitizing system 100.

The maintenance device 1300 preferably includes a portable computing device such as a laptop computer or tablet computer configured to execute logic encoded in a software application as machine code, byte code, object code, or any other machine readable instructions able to execute on a particular set of logic circuits or on any suitable operating system such as various versions of Microsoft Windows®, Microsoft Mobile®, Google Android™, Symbian OS, Palm OS, Mobile Linux, Apple OS X® (iPhone®, iPad®), and MXI. In other forms, the application used by maintenance device 1300 may be browser-based and may include embedded software, to name a few non-limiting examples. Other examples of maintenance device 1300 also include a cell phone, smart phone, or other mobile electronic device capable of communicating with sanitizing system 100 such as an iPhone®, iPad®, Blackberry®, or the like.

Maintenance device 1300 may utilize any suitable arrangement of one or more processors, microcontroller, logic gates, timers, memory circuits, and other electronic components known in the art. For example, the processor may be of the electronic variety defining digital circuitry, analog circuitry, or both. In one embodiment, the processor is of a conventional, integrated circuit microprocessor arrangement, such as one or more CORE™ processors (including CORE 2 Duo, Core i3, Core i7 and the like) or PENTIUM 4® processors supplied by INTEL Corporation of Santa Clara, Calif., USA. It shall be appreciated that other processors manufactured by INTEL or other suppliers would be suitable for use with the system and method described herein. Likewise, one or more microcontrollers such as those commercially available from Microchip Technology Inc., of Chandler, Ariz., USA may also be programmed with control logic for operating maintenance device 1300 as well.

Maintenance device 1300 may also include one or more types of solid-state electronic memory, magnetic memory, or optical memory, just to name a few. By way of non-limiting example, each memory may include solid-state electronic Random Access Memory (RAM), Sequentially Accessible Memory (SAM) (such as the First-In, First-Out (FIFO) variety or the Last-In-First-Out (LIFO) variety), Programmable Read Only Memory (PROM), Electronically Programmable Read Only Memory (EPROM), or Electrically Erasable Programmable Read Only Memory (EEPROM); an optical disc memory (such as a DVD or CD ROM); a magnetically encoded hard disc, floppy disc, tape, or cartridge media; or a combination of any of these memory types. Also, each memory may be volatile, nonvolatile, or a hybrid combination of volatile and nonvolatile varieties. The memory may also contain computer-readable instructions which are programmed or otherwise configured to direct the processor to perform the functionality of the maintenance device 1300.

When maintenance device 1300 is connected to sanitizing system 100, a communication link can be established between controller 700 and maintenance device 1300 through maintenance device connection 708 coupled to connection port 104 and maintenance device coupling 1301. Once sanitizing system 100 and maintenance device 1300 are connected, various parameters and information can be exchanged between the two devices such as real time data, system parameters, operating parameters, historical information about sanitizing system 100, identifying information, and possibly other similar types of information saved within the controller in a memory such as memory 704 of controller 700. These value stored in the memory within controller 700 for later access or to be adjusted by maintenance device 1300 and saved back to the controller to modify the controller's operational characteristics.

Some exemplary operating parameters include a minimum time for ozone production which corresponds to the minimum time limit comparison made in step 1106 (FIG. 11). Adjusting the minimum time limit operating parameter increases or decreases the minimum amount of time that ozone generator 317 will generate ozone regardless of whether the ozone concentration setpoint or ozone hysteresis values trigger the generator to activate. (See FIG. 11) Likewise, a maximum time for ozone production may be included for comparison (such as in step 1102) to ensure that the ozone generator does not continue generating ozone well beyond a reasonable length of time determined by experimentation. Operating ozone generator 317 too long may cause premature failure of the device and other adverse consequences such as an undesirably large quantity of ozone generation byproducts inside inner chamber 200. By making these two parameters adjustable, future experimentation results can be implemented within the ozone sanitizing system by simply coupling the maintenance device 1300 to sanitizing system 100, changing the corresponding values, and saving them into the memory in controller 700.

Other operating parameters include parameters indicating the duration for the different types of sanitizing cycles. In the embodiments shown and described above, three cycles are indicated such as short (light), medium (moderate), and long (heavy cycles). However, other embodiments are envisioned having a different number of cycles such as one, two, or five cycles, or more. Operating parameters are saved by controller 700 to indicate the length of time for a given cycle. Parameters indicating the duration for a light (or short) sanitizing cycle ozone soak, such as 6 minutes, the duration for a medium sanitizing cycle ozone soak, such as 15 minutes, and the duration for a high (or long) sanitizing cycle ozone soak, such as 25 minutes can also be included to allow adjustments to these time periods using maintenance device 1300. These parameters can be used in conjunction with starting the countdown clock (see step 1009 in FIG. 10) and determining when the countdown clock has expired (see step 1108 in FIG. 11) to ensure that the sanitizing process is maintained for the proper period of time.

A peak ozone level parameter can also be set to indicate an ozone set point or a predetermined ozone concentration such as 19 ppm. This value can be used at logical steps 1101 and 1104 (see FIG. 11) to activate and deactivate the ozone generator if the ozone concentration is above or below a predetermined set point. Along with the setpoint, an ozone hysteresis level, or soak hysteresis parameter may also be included. The soak hysteresis parameter provides some additional variability in the setpoint to reduce the frequency at which ozone generator is turned on and off while maintaining a satisfactory ozone concentration.

The parameters may also include a minimum ozone conversion period and a maximum ozone conversion period for embodiments where it is advantageous to ensure that the conversion process occurs for at least a minimum period of time and not more than the maximum period of time. Other parameters such as a safe ozone level and an unlock ozone level can be set to indicate when ozone concentrations within the inner container 200 are at a level below which it is save to unlock the door. In one example embodiment, the door is not unlocked until the ozone conversion reduced the ozone concentration down to the "unlock ozone level," 0.15 ppm for example.

Along with operating parameters, the memory in controller 700 maintains one or more current state values indicating information about the current state of the running system, preferably during a sanitizing cycle, or when the machine is operating and ready to begin a sanitizing cycle (see step 800 in FIG. 8). The current state values are preferably also accessible by maintenance device 1300 and include values for current temperature, humidity, and ozone level as determined by the ozone sensor within the interior chamber 200. Other values such as the current sanitizing cycle (for example "light", "medium", or "heavy"), the cycle status which may be represented as a phase identifier indicating what phase of the cycle the system is currently operating in such as "sanitize" or "conversion", or a sanitizing cycle duration which may be represented as the current time remaining before the cycle, including generation and conversion periods, is expected to complete. In another embodiment, variables such as the total time ozone production or conversion has occurred within the given cycle are also included.

Other information may also be updated by maintenance device 1300 such as unit serial number, controller serial number, the last date the ozone sensor was installed, the last date an audit of the systems behavior was performed, a lifetime cycle count of the number of cycle the unit has completed, and the last date that service was performed to name a few possibilities. The controller logic itself may also be changed and modified to improve or upgrade the behavior implemented by controller 700. As this occurs, controller 700 may also store the version number of the software it is currently operating and provide this information to the maintenance device 1300 for updating as well. Maintenance device 1300, whether by software or by other means, may include the option to unlock the parameters mentioned above to edit them and then lock them again. It may also include the option to send and receive the parameters by requiring the operator to actuate a button on a keypad, or click a software generated icon or button on a screen. In another embodiment, however, software parameters may be automatically received and sent as they are changed by maintenance device 1300.

Figure 14:
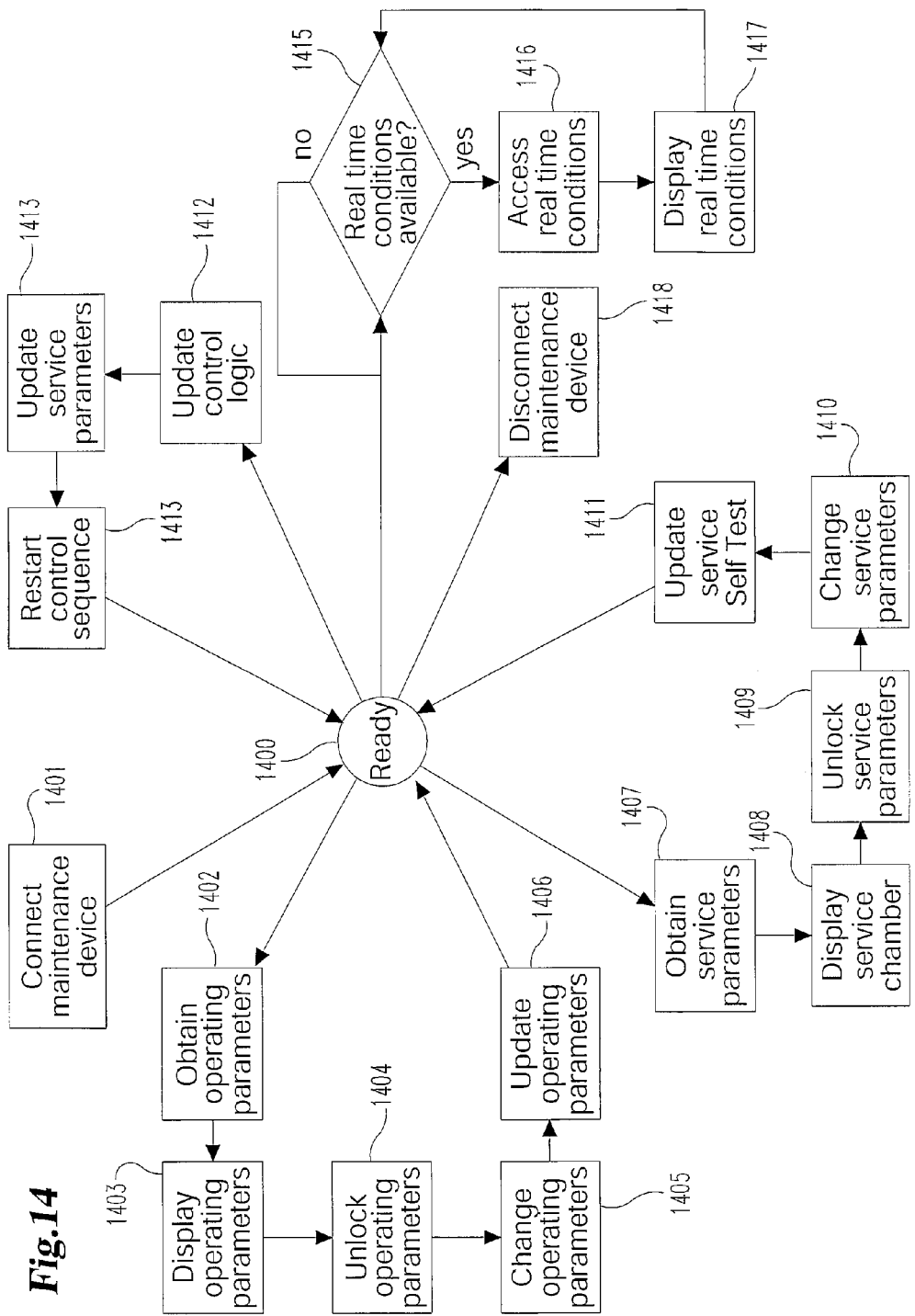
FIG. 14 is a flowchart indicating one embodiment of the logical flow of operations executed by the maintenance device of FIG. 13.

An example of the logical flow of how maintenance device 1300 may be used is illustrated in FIG. 14 where the device is at a ready state (1400) which is entered when the maintenance device (such as maintenance 1300) is connected to sanitizing system (1401). Operating parameters can be updated by first obtaining the operating parameters (1402) from the controller, displaying the operating parameters (1403) to the user of the maintenance device, unlocking the operating parameters for editing in the maintenance device where necessary (1404), and changing the operating parameters (1405). In FIG. 14, step 1404 and 1405 are performed by the maintenance device where the device has obtained operating parameter values from the sanitizing system, accepted input from the user, and is now adjusting its copy of the operating parameters to the new values input by the user. When the maintenance device has prepared the values, the operating parameters are updated in the controller (1406) thus transferring them from the maintenance device to the sanitizing system at which point the controller contains new values and the maintenance device is ready (1400) for new operations.

Service parameters are updated in a similar fashion as operating parameters. Service parameters are obtained (1407) and displayed to the user of the maintenance device (1408) and unlocked as necessary (1409). The user changes the copied values in the maintenance device and the updated service parameters are then changed to the new values and made ready for transfer (1410). The maintenance device then updates sanitizing system controller 700 with the new service parameter values (1411) leaving the maintenance device ready (1400) for another task.

In another maintenance task, the control logic is updated with a new series of logic steps (1412) preferably in the form of a program control code such as a firmware upgrade or other suitable system upgrade. Service parameters are then updated as well (1413) to indicate a new version of the control software was just installed, and the control sequence for the sanitizing system is preferably restarted (1414) leaving the maintenance device ready for other tasks (1400).

If real-time conditions are available from the sanitizing system (1415), these real-time conditions can be accessed (1416) and displayed for the user of the maintenance device (1417). Such conditions are then continuously accessed and redisplayed as long as the sanitizing system continues to provide them (1415). As shown in FIG. 14, this operation of displaying the real-time conditions if they are available preferably continues to proceed regardless of whether operating parameters and service parameters are being updated. However, there may be situations in some embodiments of the system where accessing conditions in real-time may not be possible while other operations are occurring, such as during an update of the control logic in the sanitizing system controller. Therefore in some embodiments accessing real-time conditions may be an activity triggered by request of the user using the maintenance device 1300 such as by clicking a button on a display for those cases where the maintenance device is running a maintenance program on the computer, or by pressing a button on a maintenance device that is custom-built rather than general purpose computer. This may then cause the system to read real-time conditions without allowing the user to execute any other operations.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. An ozone sanitizing system comprising:
    a container defining an interior space, the interior space being accessible by a selectively closeable opening;
    a floor within the interior space;
    a sensing device responsive to objects resting on the floor;
    an ozone generator having a generator outlet in fluid communication with the interior space, wherein the ozone generator has an ultraviolet light in fluid communication with the atmosphere, and wherein the ultraviolet light converts at least a portion of the atmosphere to ozone gas;
    an ozone converter having a converter inlet in fluid communication with the interior space;
    a timer;
    an ozone sensor in fluid communication with the interior space, and;
    a controller responsive to the ozone sensor and the timer for controlling the ozone generator and the ozone converter, wherein the controller is configured to stop ozone generation if the sensing device indicates an object resting on the floor.

2. The ozone sanitizing system of claim 1 further comprising a temperature sensor, or a humidity sensor, or any combination thereof, in fluid communication with the interior space.

3. The ozone sanitizing system of claim 1 further comprising:
    a locking mechanism configured to maintain the closeable opening in place;
    wherein the locking mechanism is responsive to the controller.

4. The ozone sanitizing system of claim 1 wherein the closeable opening is configured to substantially hermetically seal the opening.

5. The ozone sanitizing system of claim 1 wherein the controller is configured to keep the closeable opening closed while ozone concentrations within the interior space are above a predetermined level.

6. The ozone sanitizing system of claim 1 further comprising:
- a memory accessible by the controller for storing one or more operating parameters and a current sanitizing cycle, and;
- a control panel coupled to the controller, the control panel having one or more indicators for indicating at least the current sanitizing cycle.

7. The ozone sanitizing system of claim 6 wherein the memory is configured to store one or more current state values including a current temperature measured by a temperature sensor in fluid communication with the interior space, a current humidity measured by a humidity sensor in fluid communication with the interior space, a current ozone concentration measured by the ozone sensor, a sanitizing cycle, a total time of ozone production, a total time of ozone conversion, a sanitizing cycle duration, or any combination thereof.

8. The ozone sanitizing system of claim 6 further comprising a coupling device coupled to the controller for coupling the controller to a maintenance device operable to adjust one or more operating parameters.

9. The ozone sanitizing system of claim 8, wherein the coupling device includes a wireless connection between the maintenance device and the controller.

10. An ozone sanitizing system comprising:
- a container defining an interior space, the interior space being accessible by a selectively closeable opening, wherein the container is substantially hermetically sealed when the selectively closeable opening is closed;
- an ozone generator having a generator outlet in fluid communication with the interior space, wherein the generator is configured to convert diatomic oxygen in at least a portion of the atmosphere to ozone gas;
- an ozone converter having a converter inlet in fluid communication with the interior space, wherein the ozone converter is configured to convert ozone gas to diatomic oxygen when the container is substantially hermetically sealed;
- a timer;
- an ozone sensor in fluid communication with the interior space;
- a controller responsive to the ozone sensor and the timer for controlling the ozone generator, the ozone converter, and the selectively closeable opening, wherein the controller is configured to control the ozone generator to produce ozone gas when the container is substantially hermetically sealed;
- a memory accessible by the controller for storing one or more operating parameters and a current sanitizing cycle;
- a control panel coupled to the controller, the control panel having one or more indicators for indicating at least the current sanitizing cycle; and
- a coupling device coupled to the controller for coupling the controller to a maintenance device operable to adjust one or more operating parameters.

11. The ozone sanitizing system of claim 10, wherein the ozone generator includes an ultraviolet light in fluid communication with the atmosphere in the container, and wherein the diatomic oxygen in a portion of the atmosphere is converted to ozone using the ultraviolet light.

12. The ozone sanitizing system of claim 10, wherein the ozone generator includes a cold plasma generator in fluid communication with the atmosphere in the container, and wherein the diatomic oxygen in a portion of the atmosphere is converted to ozone using the cold plasma generator.

13. The ozone sanitizing system of claim 10, wherein the ozone generator is configured to produce ozone gas by electrolytic ozone generation that includes splitting water into hydrogen, diatomic oxygen, and ozone gas.

14. The ozone sanitizing system of claim 10 further comprising a temperature sensor, or a humidity sensor, or any combination thereof, in fluid communication with the interior space.

15. The ozone sanitizing system of claim 10 further comprising:
- a locking mechanism configured to maintain the selectively closeable opening in a closed state, wherein the locking mechanism is responsive to the controller.

16. The ozone sanitizing system of claim 10 further comprising
- a floor within the interior space, and;
- a sensing device responsive to objects resting on the floor;
- wherein the controller is configured to stop ozone generation if the sensing device indicates an object resting on the floor.

17. The ozone sanitizing system of claim 10 wherein the controller is configured to keep the closeable opening closed while ozone concentrations within the interior space are above a predetermined level.

18. The ozone sanitizing system of claim 10, wherein the coupling device includes a wireless connection between the maintenance device and the controller.

19. An ozone sanitizing system comprising:
- a container defining an interior space, the interior space being accessible by a selectively closeable opening;
- an ozone generator having a generator outlet in fluid communication with the interior space, wherein the ozone generator converts at least a portion of the atmosphere to ozone gas by any of an ultraviolet light, a cold plasma generator, or electrolytic ozone generation that includes splitting water into hydrogen, diatomic oxygen, and ozone gas;
- an ozone converter having a converter inlet in fluid communication with the interior space;
- a timer;
- an ozone sensor in fluid communication with the interior space;
- a controller responsive to the ozone sensor and the timer for controlling the ozone generator and the ozone converter
- a memory accessible by the controller for storing one or more operating parameters;
- a control panel coupled to the controller, the control panel having one or more indicators for indicating at least a current sanitizing cycle; and
- a coupling device coupled to the controller for coupling the controller to a maintenance device operable to adjust the one or more operating parameters.

20. The ozone sanitizing system of claim 19 further comprising
- a floor within the interior space, and;
- a sensing device responsive to objects resting on the floor;
- wherein the controller is configured to stop ozone generation if the sensing device indicates an object resting on the floor.

21. The ozone sanitizing system of claim 19 wherein the controller is configured to keep the closeable opening closed while ozone concentrations within the interior space are above a predetermined level.

22. The ozone sanitizing system of claim 19 further comprising
- a temperature sensor and a humidity sensor in fluid communication with the interior space;

wherein the memory is configured to store one or more current state values including a current temperature measured by the temperature sensor, a current humidity measured by the humidity sensor, a current ozone concentration measured by the ozone sensor, the current sanitizing cycle, a total time of ozone production, a total time of ozone conversion, a sanitizing cycle duration, or any combination thereof.

23. The ozone sanitizing system of claim 19, wherein the coupling device includes a wireless connection between the maintenance device and the controller.

* * * * *